(12) United States Patent
Komatsu et al.

(10) Patent No.: US 9,428,809 B2
(45) Date of Patent: Aug. 30, 2016

(54) SOLID-PHASE CARRIER FOR AMINATED OLIGONUCLEOTIDE

(75) Inventors: Yasuo Komatsu, Hokkaido (JP); Naoshi Kojima, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 135 days.

(21) Appl. No.: 14/238,351

(22) PCT Filed: Jul. 31, 2012

(86) PCT No.: PCT/JP2012/069381
§ 371 (c)(1),
(2), (4) Date: Feb. 11, 2014

(87) PCT Pub. No.: WO2013/024694
PCT Pub. Date: Feb. 21, 2013

(65) Prior Publication Data
US 2014/0187724 A1     Jul. 3, 2014

(30) Foreign Application Priority Data
Aug. 12, 2011 (JP) ................................ 2011-177186

(51) Int. Cl.
C07H 21/02 (2006.01)
C07H 21/00 (2006.01)
C07H 21/04 (2006.01)
C12Q 1/68 (2006.01)

(52) U.S. Cl.
CPC ............. *C12Q 1/6876* (2013.01); *C07H 21/00* (2013.01); *C07H 21/04* (2013.01)

(58) Field of Classification Search
None
See application file for complete search history.

(56) References Cited

U.S. PATENT DOCUMENTS 7,491,857 B2 *  2/2009  Komatsu ............. C07F 9/65586
                                                    570/157
2008/0227968 A1  9/2008  Komatsu et al.

FOREIGN PATENT DOCUMENTS

JP  2007-28993  2/2007
JP  4336820     7/2009

OTHER PUBLICATIONS

Kojima et al., "Efficient synthesis of oligonucleotide conjugates on solid-support using an (aminoethyoxycarbonyl)aminohexyl group for 5' terminal modification" 19 Bioorganic & Medicinal Chemistry Letters 2144-2147 (2009).*

Petrie, Charles R., et al., "An Improved CPG Support for the Synthesis of 3'-Amine-Tailed Oligonucleotides", Bioconjugate Chemistry, 1992, vol. 3, pp. 85-87.

Lyttle, Matthew H., et al., "Versatile Linker Chemistry for Synthesis of 3'-Modified DNA", Bioconjugate Chemistry, 1997, vol. 8, pp. 193-198.

Komatsu, Yasuo, et al., "Novel Amino Linkers Enabling Efficient Labeling and Convenient Purification of Amino-Modified Oligonucleotides", Bioorganic & Medicinal Chemistry, 2008, vol. 16, pp. 941-949.

Drioli, Sara, et al., "Liquid-Phase Synthesis and Characterization of a Conjugated Chimeric Oligonucleotide-PEG-Peptide", European Journal of Organic Chemistry, Oct. 1, 2002, vol. 2002, No. 20, pp. 3473-3480.

* cited by examiner

*Primary Examiner* — Nancy J Leith
(74) *Attorney, Agent, or Firm* — McCarter & English

(57) ABSTRACT

Provided are a solid-phase carrier for solid-phase synthesis of nucleic acid having improved amino group reactivity, and an aminated oligonucleotide to which an amino group has been attached. The present invention relates to an aminated oligonucleotide represented by formula (I).

10 Claims, 10 Drawing Sheets

Oligonucleotide

Comparative Example 1 (C6)

Comparative Example 2 (ssH)

Example 1 (revH)

Example 2 (revPro)

Oligonucleotide

Example 1 (revH)

Example 2 (revPro)

Example 4 (revMe)

Example 5 (revMeOH)

SOLID-PHASE CARRIER FOR AMINATED OLIGONUCLEOTIDE

CROSS-REFERENCE TO RELATED APPLICATIONS

This application is a national stage application under 35 U.S.C. §371 of PCT/JP2012/069381, filed Jul. 31, 2012, which claims benefit of Japanese Appl. No. 2011-177186, filed Aug. 12, 2011, which is incorporated herein by reference.

SEQUENCE LISTING

The Sequence Listing associated with this application is filed in electronic format via EFS-Web and hereby is incorporated by reference into the specification. The name of the text file containing the Sequence Listing is Seq_List_119244-00068_ST25.txt. The size of the text file is 1 KB, and the text file was created on Feb. 7, 2014.

TECHNICAL FIELD

The present invention relates to a solid-phase carrier for solid-phase nucleic acid synthesis intended for adding a highly reactive amino group to the end of an oligonucleotide, and an aminated oligonucleotide with such an amino group added thereto.

BACKGROUND ART

Chemically synthesized DNAs and RNAs (hereinafter, referred to as synthesized nucleic acids) have received attention as probes for genetic analysis as well as pharmaceutical drugs. Use of the synthesized nucleic acids for these purposes requires binding these synthesized nucleic acids to, for example, solids (e.g., glass, plastics, or polymers) or functional molecules (e.g., fluorescent materials, polyethylene glycol, or peptides). Covalent bonds via amino groups introduced in the synthesized nucleic acids are widely used in the formation of this binding.

An amino group is introduced to the 5' or 3' end of each synthesized nucleic acid at the preparation stage of the synthesized nucleic acid so as not to inhibit its interaction with a nucleic acid complementary thereto and/or a nucleic acid-binding protein. The synthesized nucleic acid is typically prepared by nucleic acid strand extension in a direction from the 3' end toward the 5' end. The introduction of an amino group to the 5' end is therefore carried out by the binding of an amino group-containing amidite reagent thereto at the final stage of nucleic acid synthesis. On the other hand, the introduction of an amino group to the 3' end is carried out by the sequential synthesis of nucleic acids on a solid-phase carrier bound in advance with amino groups.

Heretofore, a compound containing an amino group bound to the end of a linear hydrocarbon group has been widely used in the amino group introduction to the 3' end (Non Patent Literatures 1 and 2). The amino group introduced using such a compound, however, is low reactive due to the simple structure in which the amino group is bound to the linear hydrocarbon group. Thus, use of this amino group produces insufficient efficiency of binding between the synthesized nucleic acid and a functional molecule or immobilization of the synthesized nucleic acid onto a solid. For this reason, an excessive amount of the reagent must be used to compensate for the low reactivity, resulting in an undesired rise in chemical modification cost for the synthesized nucleic acid.

In order to solve these problems, the present inventors have developed a technique of introducing highly reactive amino groups to synthesized nucleic acids and consequently successfully developed an oligonucleotide probe having an amino group and a carbamate structure (Patent Literature 1).

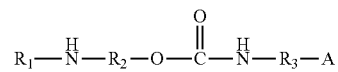

As shown in the above general formula, this oligonucleotide probe has an amino linker moiety consisting of an amino group-alkyl group (linking group)-oxycarbonylamino structure (hereinafter, referred to as an aminoalkyloxycarbonylamino structure). By virtue of this feature, the amino group of the oligonucleotide probe described in Patent Literature 1 can be bound with a molecule of interest with high binding efficiency and/or immobilization efficiency, compared with amino groups introduced in synthesized nucleic acids by the conventional techniques (Patent Literature 1 and Non Patent Literature 3).

CITATION LIST

Patent Literature

Patent Literature 1: JP Patent No. 4336820

Non Patent Literature

Non Patent Literature 1: Petrie, C. R., Reed, M. W., Adams, D., and Meyer, R. B. (1992) Bioconjugate Chem., 3, 85-87.
Non Patent Literature 2: Lyttle, M. H., Adams, H., Hudson, D., and Cook, R. M. (1997) Bioconjug Chem, 8, 193-198.
Non Patent Literature 3: Komatsu, Y., Kojima, N., Sugino, M., Mikami, A., Nonaka, K., Fujinawa, Y., Sugimoto, T., Sato, K., Matsubara, K. and Ohtsuka, E. (2008) Bioorg. Med. Chem., 16, 941-949.

SUMMARY OF INVENTION

Technical Problem

The solid-phase synthesis of synthesized nucleic acids typically involves heating treatment under alkaline conditions for the excision of nucleic acids from a carrier material and a base deprotection step, after the completion of a nucleic acid strand extension step. Unfortunately, the oligonucleotide probe described in Patent Literature 1 causes the partial decomposition or isomerization of the aminoalkyloxycarbonylamino structure, when heated under alkaline conditions without the protection of its amino group with an organic group such as a trityl group.

The 5'-end application of the amino linker moiety described in Patent Literature 1 permits protection of the amino group with an appropriate protective group. The resulting oligonucleotide probe can therefore avoid being decomposed in the deprotection step. By contrast, the 3'-end application of the amino linker moiety does not permit protection of the amino group. A product contaminated with a decomposition product caused by the reaction is therefore obtained after the nucleic acid excision from a carrier material and the base deprotection step.

In addition to the instability problem attributed to the aminoalkyloxycarbonylamino structure, a solid-phase carrier for 3'-end modification having the amino linker moiety is disadvantageously synthesized at high production cost by time-consuming steps.

In light of these problems, there has been a strong demand for the development of a novel solid-phase carrier for 3'-amino linker introduction that has both of the high reactivity of an amino group and the high stability of the whole molecule and is produced at reduced cost, and an aminated oligonucleotide having such a 3'-amino linker.

Hence, an object of the present invention is to provide a solid-phase carrier for solid-phase nucleic acid synthesis having the improved reactivity of an amino group, and an aminated oligonucleotide with such an amino group added thereto.

Solution to Problem

The present inventors have conducted diligent studies on solutions to the problems described above and consequently completed the present invention by finding that use of an amino linker having an amino group-alkyl group (linking group)-aminocarbonyloxy structure in a solid-phase carrier drastically improves stability under alkaline conditions and produces a highly reactive amino group, compared with the oligonucleotide probe described in Patent Literature 1.

Specifically, the present invention is summarized as follows:

(1) An aminated oligonucleotide represented by the following formula I:

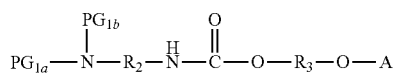
(I)

wherein $PG_{1a}$ and $PG_{1b}$ are each independently a hydrogen atom or a protective group for the amino group, or $PG_{1a}$ and $PG_{1b}$ together form a protective group for the amino group;

$R_2$ is a substituted or unsubstituted divalent aliphatic hydrocarbon group having 1 to 10 members in the main chain, or a divalent alicyclic group having 1 to 10 members in the main chain and having 3 to 20 ring members (these groups each optionally comprise one or more heteroatoms), and $R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms), or $R_2$ and $R_3$, together with the carbamate group to which they are bound, form a substituted or unsubstituted alicyclic group having 5 to 10 ring members (provided that $R_2$ and $R_3$ each independently have 1 to 10 members in the main chain); and A is an oligonucleotide.

(2) The aminated oligonucleotide according to (1), wherein $R_2$ is an unsubstituted divalent aliphatic hydrocarbon group having 1 to 5 members in the main chain.

(3) The aminated oligonucleotide according to (1), wherein $R_2$ is represented by the following formula II:

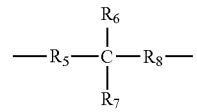
(II)

wherein $R_5$ is a direct bond or a substituted or unsubstituted 1- to 9-membered alkylene group;

$R_6$ and $R_7$ are each independently a hydrogen atom, halogen, a hydroxyl group, a substituted or unsubstituted amino group, a nitro group, a cyano group, a carboxyl group, an amide group, a substituted or unsubstituted $C_1$ to $C_{20}$ alkyl group, $C_2$ to $C_{20}$ alkenyl group, or $C_2$ to $C_{20}$ alkynyl group, a substituted or unsubstituted $C_1$ to $C_{20}$ alkoxyl group, or a substituted or unsubstituted $C_3$ to $C_{20}$ cycloalkyl group or $C_3$ to $C_{20}$ heterocyclyl group; and $R_8$ is a direct bond or a substituted or unsubstituted 1- to 5-membered alkylene group.

(4) The aminated oligonucleotide according to (1), wherein $R_2$ is represented by the following formula III:

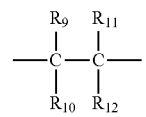
(III)

wherein $R_9$, $R_{10}$, $R_{11}$, and $R_{12}$ are each independently a hydrogen atom, halogen, a substituted or unsubstituted $C_1$ to $C_{10}$ alkyl group, $C_2$ to $C_{10}$ alkenyl group, or $C_2$ to $C_{10}$ alkynyl group, or a substituted or unsubstituted $C_1$ to $C_{10}$ alkoxyl group, or $R_9$ or $R_{10}$ and $R_{11}$ or $R_{12}$, together with the carbon atoms to which they are bound, form a substituted or unsubstituted alicyclic group having 3 to 20 ring members and optionally containing heteroatom(s).

(5) The aminated oligonucleotide according to any of (1) to (4), wherein the aminated oligonucleotide is represented by the following formula Ia:

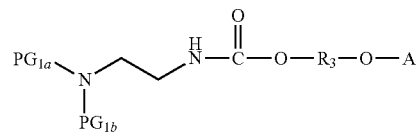
(Ia)

wherein $PG_{1a}$ and $PG_{1b}$ are each independently a hydrogen atom or a protective group for the amino group, or $PG_{1a}$ and $PG_{1b}$ together form a protective group for the amino group;

$R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms); and A is an oligonucleotide.

(6) A solid-phase carrier represented by the following formula IV:

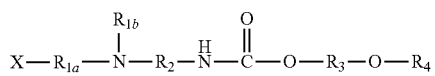
(IV)

wherein
X is a carrier material;
$R_{1a}$ is a direct bond or a divalent group, and
$R_{1b}$ is a hydrogen atom, or
$R_{1a}$ and $R_{1b}$ together form a group bound to X and the amino group;
$R_2$ is a substituted or unsubstituted divalent aliphatic hydrocarbon group having 1 to 10 members in the main chain, or a divalent alicyclic group having 1 to 10 members in the main chain and having 3 to 20 ring members (these groups each optionally comprise one or more heteroatoms), and
$R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms), or
$R_2$ and $R_3$, together with the carbamate group to which they are bound, form a substituted or unsubstituted alicyclic group having 5 to 10 ring members (provided that $R_2$ and $R_3$ each independently have 1 to 10 members in the main chain); and
$R_4$ is a protective group for the hydroxy group.

(7) The solid-phase carrier according to (6), wherein $R_2$ is an unsubstituted divalent aliphatic hydrocarbon group having 1 to 5 members in the main chain.

(8) The solid-phase carrier according to (6), wherein $R_2$ is represented by the following formula II:

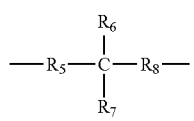
(II)

wherein
$R_5$ is a direct bond or a substituted or unsubstituted 1- to 9-membered alkylene group;
$R_6$ and $R_7$ are each independently a hydrogen atom, halogen, a hydroxyl group, a substituted or unsubstituted amino group, a nitro group, a cyano group, a carboxyl group, an amide group, a substituted or unsubstituted $C_1$ to $C_{20}$ alkyl group, $C_2$ to $C_{20}$ alkenyl group, or $C_2$ to $C_{20}$ alkynyl group, a substituted or unsubstituted $C_1$ to $C_{20}$ alkoxyl group, or a substituted or unsubstituted $C_3$ to $C_{20}$ cycloalkyl group or $C_3$ to $C_{20}$ heterocyclyl group; and
$R_8$ is a direct bond or a substituted or unsubstituted 1- to 5-membered alkylene group.

(9) The solid-phase carrier according to (6), wherein $R_2$ is represented by the following formula III:

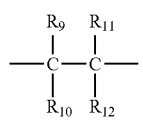
(III)

wherein
$R_9$, $R_{10}$, $R_{11}$, and $R_{12}$ are each independently a hydrogen atom, halogen, a substituted or unsubstituted $C_1$ to $C_{10}$ alkyl group, $C_2$ to $C_{10}$ alkenyl group, or $C_2$ to $C_{10}$ alkynyl group, or a substituted or unsubstituted $C_1$ to $C_{10}$ alkoxyl group, or
$R_9$ or $R_{10}$ and $R_{11}$ or $R_{12}$, together with the carbon atoms to which they are bound, form a substituted or unsubstituted alicyclic group having 3 to 20 ring members and optionally containing heteroatom(s).

(10) The solid-phase carrier according to any of (6) to (9), wherein the solid-phase carrier is represented by the following formula IVa:

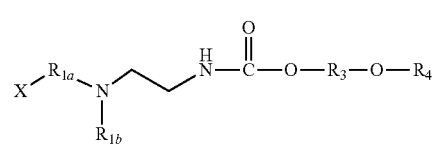
(IVa)

wherein
X is a carrier material;
$R_{1a}$ is a direct bond or a divalent group, and
$R_{1b}$ is a hydrogen atom, or
$R_{1a}$ and $R_{1b}$ together form a group bound to X and the amino group;
$R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms); and
$R_4$ is a protective group for the hydroxy group.

(11) A solid-phase carrier represented by the following formula V:

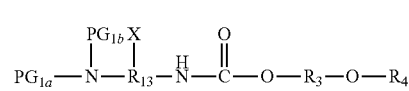
(V)

wherein
X is a carrier material;
$PG_{1a}$ and $PG_{1b}$ are each independently a hydrogen atom or a protective group for the amino group, or
$PG_{1a}$ and $PG_{1b}$ together form a protective group for the amino group;
$R_{13}$ is a substituted or unsubstituted trivalent aliphatic hydrocarbon group having 1 to 10 members in the main chain, or a trivalent alicyclic group having 1 to 10 members in the main chain and having 3 to 20 ring members (these groups each optionally comprise one or more heteroatoms), and
$R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms), or
$R_{13}$ and $R_3$, together with the carbamate group to which they are bound, form a substituted or unsubstituted alicyclic group having 5 to 10 ring members (provided that $R_2$ and $R_3$ each independently have 1 to 10 members in the main chain); and
$R_4$ is a protective group for the hydroxy group.

(12) The solid-phase carrier according to (11), wherein $R_{13}$ is a trivalent aliphatic hydrocarbon group having 1 to 5 members in the main chain.

(13) The solid-phase carrier according to any of (6) to (12), wherein $R_4$ is a trityl group or a monosubstituted or disubstituted trityl group.

(14) An aminated oligonucleotide probe represented by the following formula Ib:

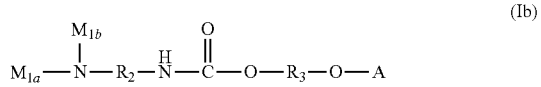

wherein $M_{1a}$ and $M_{1b}$ are each independently a hydrogen atom or a group derived from a probe molecule, or $M_{1a}$ and $M_{1b}$ together form a group derived from a probe molecule;

$R_2$ is a substituted or unsubstituted divalent aliphatic hydrocarbon group having 1 to 10 members in the main chain, or a divalent alicyclic group having 1 to 10 members in the main chain and having 3 to 20 ring members (these groups each optionally comprise one or more heteroatoms), and $R_3$ is a substituted or unsubstituted divalent aliphatic hydrocarbon group having 1 to 20 members in the main chain, or a divalent alicyclic group having 1 to 20 members in the main chain and having 3 to 20 ring members (these groups each optionally comprise one or more heteroatoms), or $R_2$ and $R_3$, together with the carbamate group to which they are bound, form a substituted or unsubstituted alicyclic group having 5 to 10 ring members (provided that $R_2$ and $R_3$ each independently have 1 to 10 members in the main chain); and A is an oligonucleotide.

Advantageous Effects of Invention

The present invention can provide a solid-phase carrier for solid-phase nucleic acid synthesis having the improved reactivity of an amino group, and an aminated oligonucleotide with such an amino group added thereto.

The present specification encompasses the contents described in the specification and/or drawings of Japanese Patent Application No. 2011-177186 on which the priority of the present application is based.

DESCRIPTION OF EMBODIMENTS

Figure 1:
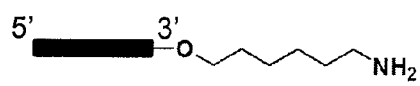
FIG. 1 is a diagram showing one embodiment of the aminated oligonucleotide of the present invention.
Figure 1:
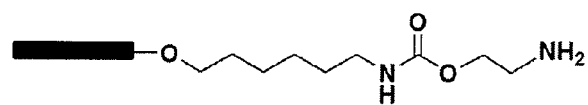
Figure 1:
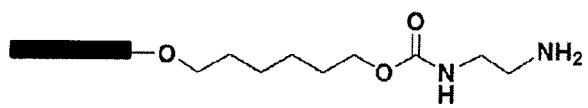
Figure 1:
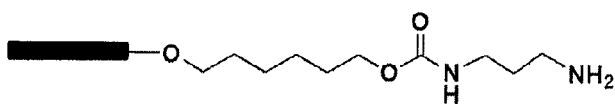

Hereinafter, preferred embodiments of the present invention will be described in detail.

<1. Aminated Oligonucleotide>

The present invention relates to an aminated oligonucleotide represented by the formula I:

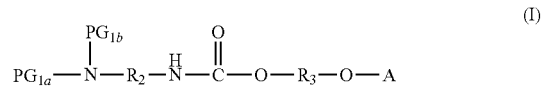

The aminated oligonucleotide of the present invention can be bound with a probe (label) molecule to produce an oligonucleotide probe for use in genetic analysis or the like. Alternatively, the aminated oligonucleotide of the present invention having a biologically active nucleic acid (e.g., antisense, aptamers, siRNAs, and microRNAs) can be bound with an organic molecule (functional molecule) that improves retention in blood or cell permeability to produce a desired nucleic acid drug.

In the present specification, the "oligonucleotide" means nucleic acids such as DNAs and RNAs, single-stranded or double-stranded oligonucleotides or polynucleotides, or their derivatives. The oligonucleotide may be natural or synthetic or may be a PCR product. Preferred examples of the oligonucleotide derivatives can include, but not limited to, oligonucleotide derivatives formed by the substitution of phosphodiester bonds in oligonucleotides with phosphorothioate bonds, oligonucleotide derivatives formed by the substitution of phosphodiester bonds in oligonucleotides with N3'-P5' phosphoramidite bonds, oligonucleotide derivatives formed by the substitution of ribose and phosphodiester bonds in oligonucleotides with peptide bonds, oligonucleotide derivatives formed by the substitution of ribose in oligonucleotides with a morpholino group, oligonucleotide derivatives formed by the replacement of uracil in oligonucleotides with C-5 propynyluracil, oligonucleotide derivatives formed by the replacement of uracil in oligonucleotides with C-5 thiazoleuracil, oligonucleotide derivatives formed by the replacement of cytosine in oligonucleotides with C-5 propynylcytosine, oligonucleotide derivatives formed by the replacement of cytosine in oligonucleotides with phenoxazine-modified cytosine, oligonucleotide derivatives formed by the replacement of ribose in oligonucleotides with 2'-O-propylribose, oligonucleotide derivatives formed by the replacement of ribose in oligonucleotides with 2'-O-methylribose, oligonucleotide derivatives formed by the replacement of ribose in oligonucleotides with 2'-fluoro-2'-deoxyribose, oligonucleotide derivatives formed by the replacement of ribose in oligonucleotides with 2'-O-4'-C-methylene-bridged ribose, oligonucleotide derivatives formed by the replacement of ribose in oligonucleotides with 2'-O-4'-C-ethylene-bridged ribose, and oligonucleotide derivatives formed by the replacement of ribose in oligonucleotides with 2'-methoxyethoxyribose.

In the present invention, the number of bases in the oligonucleotide is in the range of usually 1 to 500, preferably 5 to 200, more preferably 10 to 100.

In the present specification, the "probe (label) molecule" means a molecule routinely used in the art for labeling oligonucleotides. Examples thereof can include biotin, polyethylene glycol (PEG), fluorescent dyes, peptides, sugars, cholesterols, lipids, ferrocene, and Nile Blue. Fluorescent dyes such as CyDye (e.g., Cy3 and Cy5), fluorescein isothiocyanate (FITC), RITC, rhodamine, Texas Red, TET, TAMRA, FAM, HEX, ROX, Nile Blue, and GFP are preferred. The probe molecule may be used in an unchanged form or may be used in a form in which a group capable of forming a covalent bond with another functional group, such as active ester (e.g. succinimidyl ester), an azide group, or an alkynyl group, is introduced. Both the forms are included in the probe molecule.

In the present specification, the "amino linker" means a bridge molecule or a bridge moiety for forming a covalent bond between the oligonucleotide and a carrier material and/or the probe molecule. In the aminated oligonucleotide and the solid-phase carrier of the present invention, the amino linker moiety has an amino group-alkyl group (linking group)-aminocarbonyloxy structure formed by diamine. The aminated oligonucleotide and the solid-phase carrier of the present invention having this structure are stably present even under alkaline conditions substantially without forming a decomposition product and can provide high efficiency of modification with the probe molecule.

In the present specification, "alkyl" means a linear or branched aliphatic hydrocarbon group containing the particular number of carbon atoms. For example, "1- to 20-membered alkyl" and "$C_1$ to $C_{20}$ alkyl" each mean a linear or branched hydrocarbon chain containing at least 1 up to 20 carbon atoms. Preferred examples of alkyl can include, but not limited to, methyl, ethyl, n-propyl, isopropyl, n-butyl, sec-butyl, isobutyl, tert-butyl, n-pentyl, n-hexyl, n-heptyl, and n-octyl.

In the present specification, "alkenyl" means a group formed by the replacement of one or more C—C single bonds in the alkyl with double bonds. Preferred examples of alkenyl can include, but not limited to, vinyl, 1-propenyl, allyl, 1-methylethenyl (isopropenyl), 1-butenyl, 2-butenyl, 3-butenyl, 1-methyl-2-propenyl, 2-methyl-2-propenyl, 1-methyl-1-propenyl, 2-methyl-1-propenyl, 1-pentenyl, 1-hexenyl, n-heptenyl, and 1-octenyl.

In the present specification, "alkynyl" means a group formed by the replacement of one or more C—C single bonds in the alkyl with triple bonds. Preferred examples of alkynyl can include, but not limited to, ethynyl, 1-propynyl, 2-propynyl, 1-butynyl, 2-butynyl, 3-butynyl, 1-methyl-2-propynyl, 1-pentynyl, 1-hexynyl, 1-heptynyl, and 1-octynyl.

In the present specification, "cycloalkyl" means alicyclic alkyl containing the particular number of carbon atoms. For example, "cycloalkyl having 3 to 20 (ring) members" and "$C_3$ to $C_{20}$ cycloalkyl" each mean a cyclic hydrocarbon group containing at least 3 up to 20 carbon atoms. Preferred examples of cycloalkyl can include, but not limited to, cyclopropyl, cyclobutyl, cyclopentyl, and cyclohexyl.

In the present specification, "cycloalkenyl" means a group formed by the replacement of one or more C—C single bonds in the cycloalkyl with double bonds. Preferred examples of cycloalkenyl can include, but not limited to, cyclopropenyl, cyclobutenyl, cyclopentenyl, and cyclohexenyl.

In the present specification, "cycloalkynyl" means a group formed by the replacement of one or more C—C single bonds in the cycloalkyl with triple bonds. Preferred examples of cycloalkynyl can include, but not limited to, cyclobutynyl, cyclopentynyl, and cyclohexynyl.

In the present specification, "heterocyclyl" means a group formed by the replacement of one or more carbon atoms in the cycloalkyl, the cycloalkenyl, or the cycloalkynyl each independently with a heteroatom selected from a nitrogen atom (N), a sulfur atom (S), and an oxygen atom (O). For example, "heterocyclyl having 3 to 20 (ring) members" and "$C_3$ to $C_{20}$ heterocyclyl" each mean a group formed by the replacement of one or more carbon atoms in a cyclic hydrocarbon group containing at least 3 up to 20 carbon atoms each independently with the heteroatom. In this case, the replacement with N or S encompasses replacement with N-oxide or oxide or dioxide of S. Preferred examples of heterocyclyl can include, but not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, dioxanyl, and piperazinyl.

In the present specification, "aryl" means an aromatic group containing 5 to 20 carbon atoms. For example, "aryl having 5 to 20 (ring) members" and "$C_5$ to $C_{20}$ aryl" each mean an aromatic group containing at least 5 up to 20 carbon atoms. Preferred examples of aryl can include, but not limited to, phenyl, naphthyl, and anthryl (anthracenyl).

In the present specification, "arylalkyl" means a group formed by the replacement of one hydrogen atom in the alkyl with the aryl. Preferred examples of arylalkyl can include, but not limited to, benzyl, 1-phenethyl, and 2-phenethyl.

In the present specification, "arylalkenyl" means a group formed by the replacement of one hydrogen atom in the alkenyl with the aryl. Preferred examples of arylalkenyl can include, but not limited to, styryl.

In the present specification, "heteroaryl" means a group formed by the replacement of one or more carbon atoms in the aryl each independently with a heteroatom selected from a nitrogen atom (N), a sulfur atom (S), and an oxygen atom (O). For example, "heteroaryl having 5 to 20 (ring) members" and "$C_5$ to $C_{20}$ heteroaryl" each mean a group formed by the replacement of one or more carbon atoms in an aromatic group containing at least 5 up to 20 carbon atoms each independently with the heteroatom. In this case, the replacement with N or S encompasses replacement with N-oxide or oxide or dioxide of S. Preferred examples of heteroaryl can include, but not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridyl, pyridazinyl, pyrazinyl, pyrimidinyl, quinolinyl, isoquinolinyl, and indolyl.

In the present specification, "heteroarylalkyl" means a group formed by the replacement of one hydrogen atom in the alkyl with the heteroaryl.

In the present specification, "alkylene" means a linear or branched divalent aliphatic hydrocarbon group containing the particular number of carbon atoms. For example, "1- to 9-membered alkylene" and "$C_1$ to $C_9$ alkylene" each mean a linear or branched divalent hydrocarbon chain containing at least 1 up to 9 atoms (preferably carbon atoms). Preferred examples of alkylene can include, but not limited to, methylene, ethylene, n-propylene, isopropylene, n-butylene, sec-butylene, isobutylene, tert-butylene, and n-pentylene.

In the present specification, "alkenylene" means a divalent group formed by the replacement of one or more C—C single bonds in the alkylene with double bonds. Preferred examples of alkenylene can include, but not limited to, vinylene (ethene-1,2-diyl) and propenylene.

In the present specification, "alkynylene" means a divalent group formed by the replacement of one or more C—C single bonds in the alkylene with triple bonds. Preferred examples of alkynylene can include, but not limited to, ethyne-1,2-diyl.

The groups described above may each independently contain one or more heteroatoms selected from the group consisting of an oxygen atom, a nitrogen atom, a sulfur atom, a silicon atom, and a phosphorus atom. An oxygen atom, a nitrogen atom, or a sulfur atom is preferred. In this case, one or more carbon atoms constituting each of these groups are each independently replaced with any of these heteroatoms. Hence, the groups described above include their unchanged forms as well as forms in which one or some carbon atoms in each of the groups are replaced with heteroatoms.

The groups described above are each independently unsubstituted or may be substituted by one or more substituents selected from halogen, a hydroxyl group, a substituted or unsubstituted amino group, a nitro group, a cyano group, a carboxyl group, an amide group, and a substituted or unsubstituted monovalent hydrocarbon group optionally containing heteroatom(s) (e.g., substituted or unsubstituted $C_1$ to $C_{20}$ alkyl, $C_2$ to $C_{20}$ alkenyl, $C_2$ to $C_{20}$ alkynyl, $C_1$ to $C_{20}$ alkoxyl, $C_3$ to $C_{20}$ cycloalkyl, $C_3$ to $C_{20}$ cycloalkyloxy, $C_3$ to $C_{20}$ cycloalkenyl, $C_3$ to $C_{20}$ cycloalkenyloxy, $C_3$ to $C_{20}$ cycloalkynyl, $C_3$ to $C_{20}$ cycloalkynyloxy, $C_3$ to $C_{20}$ heterocyclyl, $C_3$ to $C_{20}$ heterocyclyloxy, $C_5$ to $C_{20}$ aryl, $C_5$ to $C_{20}$ aryloxy, $C_6$ to $C_{20}$ arylalkyl, $C_6$ to $C_{20}$ arylalkenyl, $C_5$ to $C_{20}$ heteroaryl, $C_5$ to $C_{20}$ heteroaryloxy, or $C_6$ to $C_{20}$ heteroarylalkyl, wherein one or some carbon atoms in each of these groups may be replaced with heteroatoms). In this case, these groups may each independently be further substituted by one or more of the groups.

In the present specification, "halogen" or "halo" means fluorine, chlorine, bromine, or iodine.

As already described, the oligonucleotide probe described in Patent Literature 1 is unstable under alkaline conditions, which are used in the excision of an oligonucleotide from a solid-phase carrier in solid-phase oligonucleotide synthesis. The present inventors have found that the aminated oligonucleotide represented by the formula I is stably present even under such alkaline conditions substantially without forming a decomposition product and is highly reactive with a probe molecule. This feature permits the introduction of an amino group into the 3' end of an oligonucleotide, which has been difficult to achieve for the oligonucleotide probe described in Patent Literature 1.

In the formula I, A is an oligonucleotide. The oligonucleotide defined above is preferred. A forms a covalent bond (ether bond (C—O—C) or phosphoester bond ($PO_2$—O—C)) via the oxygen atom bound to $R_3$, at the carbon atom of the 5'- or 3'-end of the oligonucleotide or a phosphorus atom in a phosphate group bound to the carbon atom.

For the introduction of an amino group to the 3' end of an oligonucleotide, first, an amino linker is synthesized and bound with a carrier material to synthesize a solid-phase carrier comprising the amino linker moiety. Subsequently, nucleic acids are sequentially synthesized on the solid-phase carrier. The binding between the amino linker and the carrier material is usually formed via the terminal amino group of the amino linker. The synthesis of the amino linker described in Patent Literature 1 requires forming a carbamate group with the terminal amino group protected, for preventing side reaction. The binding of the carrier material to the terminal amino group of the amino linker therefore requires two steps of deprotecting the protective group for the terminal amino group and then binding the carrier material thereto (scheme 2 of Comparative Example 2 described below). By contrast, the synthesis of the amino linker of the present invention employs diamine as a starting material and can therefore form a carbamate group with the terminal amino group in a free form (i.e., unprotected form). For this reason, the deprotection step is unnecessary after the formation of the carbamate group. Thus, the binding between the amino linker and the carrier material can be achieved by one step (scheme 1 of Synthesis Example 1 described below).

In the case of using the aminated oligonucleotide described in Patent Literature 1 in the 3'-end modification of the oligonucleotide, the terminal amino group may cause nucleophilic attack of a carbonyl carbon atom in the carbamate group under alkaline conditions used in the excision of the oligonucleotide from a solid-phase carrier. This nucleophilic attack by the terminal amino group cleaves the carbon-nitrogen bond or the carbon-oxygen bond in the carbamate group. In the former case, a cyclic carbamate compound and an amine adduct of the oligonucleotide are formed. In the latter case, intramolecular transfer occurs to form a transfer product as a result of conversion of the carbamate group into a urea group. None of these products can form the original aminated oligonucleotide under the same alkaline conditions as above. For this reason, the aminated oligonucleotide described in Patent Literature 1 cannot be stably present under alkaline conditions, so that the products accumulate as decomposition products in the reaction system.

In the case of using the aminated oligonucleotide represented by the formula I of the present invention in the 3'-end modification of the oligonucleotide, similar reaction may also occur under alkaline conditions. Specifically, the nucleophilic attack by the terminal amino group cleaves the carbon-oxygen bond or the carbon-nitrogen bond in the carbamate group. In the former case, cyclic urea and a diol adduct of the oligonucleotide are formed. In the latter case, intramolecular transfer (hereinafter, referred to as "transacylation") occurs to form a transacylation product as a result of the conversion of the NH moiety of the carbamate group into a terminal amino group. Of these products, the transacylation product can form the aminated oligonucleotide represented by the formula I through re-transacylation reaction. For this reason, the aminated oligonucleotide represented by the formula I of the present invention can be more stably present than the aminated oligonucleotide described in Patent Literature 1 under alkaline conditions used in the oligonucleotide excision from a solid-phase carrier.

Hence, the aminated oligonucleotide represented by the formula I of the present invention preferably has a covalent bond formed via the oxygen atom bound to $R_3$, at the 3' end of the oligonucleotide represented by A. Use of the amino linker of the present invention in the 3'-end modification of the oligonucleotide allows the aminated oligonucleotide to be produced at high yields using a fewer steps, compared with use of the amino linker described in Patent Literature 1.

In the formula I, $PG_{1a}$ and $PG_{1b}$ are each independently a hydrogen atom or a protective group for the amino group, or $PG_{1a}$ and $PG_{1b}$ together form a protective group for the amino group. Examples of the protective group for the amino group in $PG_{1a}$ and $PG_{1b}$ can include, but not limited to, an acetyl group, a trifluoroacetyl group, a benzoyl group, a 9-fluorenylmethyloxycarbonyl group, a phthaloyl group, an o-nitrobenzyl group, and an o-nitrobenzyloxycarbonyl group.

$R_2$ and $R_3$ are each independently a divalent group. $R_2$ and $R_3$ are not particularly limited unless inhibiting binding ability against a solid and the complementary binding between the oligonucleotide and a target oligonucleotide. A substituted or unsubstituted divalent hydrocarbon group optionally containing heteroatom(s) is preferred.

$R_2$ is preferably a divalent group containing 1 to 10, preferably 1 to 5, more preferably 2 carbon atoms or heteroatoms in the shortest chain that connects the nitrogen atoms of the amino groups bound to both ends (hereinafter, referred to as the main chain). The length of the main chain in $R_2$ is set to the above range to keep the distance between the carbamate group and the amino group within a fixed range. This can reduce the basicity (pKa) of the amino group and inhibit the protonation of the amino group, thereby improving the reactivity of the amino group.

Preferred examples of $R_2$ can include, but not limited to, a substituted or unsubstituted divalent aliphatic hydrocarbon group having 1 to 10, preferably 1 to 5, more preferably 2 members in the main chain, a substituted or unsubstituted divalent alicyclic group having 1 to 10, preferably 1 to 5 members in the main chain and having 3 to 20 ring members, and a substituted or unsubstituted divalent aromatic group having 5 to 20 ring members. A substituted or unsubstituted $C_1$ to $C_{10}$ alkylene group, $C_2$ to $C_{10}$ alkenylene group, or $C_2$ to $C_{10}$ alkynylene group is preferred. These groups may each contain one or more heteroatoms. Particularly preferred examples of $R_2$ can include methylene, ethylene, and propylene. Ethylene is preferred.

$R_2$ is particularly preferably an unsubstituted divalent linear aliphatic hydrocarbon group having 1 to 10, preferably 1 to 5, more preferably 2 members in the main chain, or an unsubstituted divalent alicyclic group having 1 to 10, preferably 1 to 5, more preferably 2 members in the main chain and having 3 to 20 ring members (these groups each optionally comprise one or more heteroatoms). An unsubstituted $C_1$ to $C_5$ linear alkylene group, $C_2$ to $C_5$ linear alkenylene group, or $C_2$ to $C_5$ linear alkynylene group is preferred. In the divalent aromatic group represented by $R_2$, the length of the main chain is determined depending on the number of ring atoms in the aromatic group. This may increase the distance between the carbamate group and the amino group, thereby reducing the reactivity of the amino group. Hence, the aliphatic hydrocarbon group represented by $R_2$ can keep the distance between the carbamate group and the amino group within a fixed range, thereby improving the reactivity of the amino group.

As described above, the aminated oligonucleotide represented by the formula I of the present invention may cause transacylation reaction under alkaline conditions. When $R_2$ is, for example, alkylene having 2 members in the main chain and is a group that has a branched chain or a substituent described below, the branched moiety (hereinafter, also referred to as a "branch group") or the substituent in $R_2$ takes stable anti-conformation against the terminal amino group by steric hindrance during the reaction process of the transacylation. In this case, the terminal amino group is located in proximity to the carbonyl carbon atom of the carbamate group. Thus, the transacylation reaction can be promoted. Such promotion of the transacylation reaction attributed to the steric hindrance of the branch group and/or the substituent in $R_2$ may also presumably occur in other groups represented by $R_2$. The conformational equilibrium described above may vary depending on the degree of the steric hindrance of the branch group or the substituent. $R_2$ having a bulky branch group or substituent with large steric hindrance (e.g., a substituted, branched and/or long-chain aliphatic hydrocarbon group or aromatic group, for example, hydroxymethyl, methoxymethyl, phenyl, naphthyl, or naphthylmethoxymethyl) further promotes the transacylation reaction, compared with $R_2$ having a branch group or a substituent with small steric hindrance (unsubstituted 1- to 5-membered linear aliphatic hydrocarbon group, for example, methyl or ethyl).

By contrast, the linear and unsubstituted divalent aliphatic hydrocarbon group represented by $R_2$ has the minimum steric hindrance. Thus, the conformational equilibrium does not largely shift toward anti-conformation. Also, $R_2$ has a symmetric structure. In this case, apparently, no structural change occurs even if transacylation reaction takes place. This means that the resulting transacylation product has the same structure as that before the transfer. Thus, apparently, no structural change occurs even if transacylation takes place.

Hence, $R_2$ is preferably in an unsubstituted form or a form having a substituent with small steric hindrance (unsubstituted 1- to 5-membered linear aliphatic hydrocarbon group, for example, methyl or ethyl), more preferably in an unsubstituted and linear form. The group of $R_2$ in an unsubstituted and linear form can substantially suppress reduction in yield caused by transacylation even under alkaline conditions.

$R_3$ is preferably a divalent group containing 1 to 20, preferably 2 to 15, more preferably 2 to 6 carbon atoms or heteroatoms in the shortest chain that connects the oxygen atom of the carbamate group and the terminal oxygen atom (hereinafter, referred to as the main chain). The length of the main chain in $R_3$ that falls within the above range probably has no substantial influence on the reactivity of the amino group and the stability of the aminated oligonucleotide.

Preferred examples of $R_3$ can include, but not limited to, a substituted or unsubstituted divalent aliphatic hydrocarbon group having 1 to 20, preferably 2 to 15, more preferably 2 to 6 members in the main chain, a substituted or unsubstituted divalent alicyclic group having 1 to 20, preferably 2 to 15, more preferably 2 to 6 members in the main chain and having 3 to 20 ring members, and a substituted or unsubstituted divalent aromatic group having 5 to 20 ring members. A substituted or unsubstituted $C_1$ to $C_{10}$ alkylene group, $C_2$ to $C_{10}$ alkenylene group, and $C_2$ to $C_{10}$ alkynylene group are preferred. These groups may each contain one or more heteroatoms. Particularly preferred examples of $R_3$ can include ethylene, propylene, butylene, pentylene, hexylene, phenylene, and naphthylene. Hexylene is preferred.

$R_3$ is particularly preferably an unsubstituted divalent linear aliphatic hydrocarbon group having 1 to 20, preferably 2 to 15, more preferably 2 to 6 members in the main chain, or a divalent alicyclic group having 1 to 20, preferably 2 to 15, more preferably 2 to 6 members in the main chain and having 3 to 20 ring members (these groups each optionally comprise one or more heteroatoms). $R_3$ is preferably an unsubstituted linear $C_1$ to $C_{20}$ alkylene group, $C_2$ to $C_{20}$ alkenylene group, or $C_2$ to $C_{20}$ alkynylene group, more preferably an unsubstituted linear $C_1$ to $C_{10}$ alkylene group, $C_2$ to $C_{10}$ alkenylene group, or $C_2$ to $C_{10}$ alkynylene group, further preferably an unsubstituted linear $C_2$ to $C_6$ alkylene group, $C_2$ to $C_6$ alkenylene group, or $C_2$ to $C_6$ alkynylene group. These groups represented by $R_3$ can keep the distances between the oligonucleotide and the carbamate group and between the oligonucleotide and the terminal amino group within fixed ranges. This can improve, for example, the efficiency of detection of a probe molecule substantially without inhibiting the detection reaction of the probe molecule in the case of preparing an oligonucleotide probe by the introduction of a group derived from the probe molecule to the terminal amino group.

Alternatively, $R_2$ and $R_3$, together with the carbamate group to which they are bound, may form a ring. The ring formed by $R_2$ and $R_3$ is preferably a substituted or unsubstituted alicyclic group or aromatic group having 5 to 10, preferably 5 or 6 ring members and optionally containing one or more heteroatoms, more preferably 4,5-dihydrooxazol-2(3H)-one-4,5-diyl. In this case, a preferred combination is $R_2$ having 1 to 10, preferably 1 to 5, more preferably 2 members in the main chain and $R_3$ having 1 to 10, preferably 2 to 6, more preferably 2 members in the main chain.

In the formula I, $R_2$ and $R_3$ may each independently be substituted by one or more of the substituents defined above. Preferred examples of the substituents can include, but not limited to, naphthylmethoxymethyl, methoxymethyl, methyl, hydroxymethyl, hydroxyethyl, and fluorine. In consideration of the possible transacylation described above, however, $R_2$ and $R_3$ are each independently preferably in an unsubstituted form or a form having a substituent with small steric hindrance (unsubstituted 1- to 5-membered linear aliphatic hydrocarbon group, for example, methyl or ethyl), more preferably in an unsubstituted form. The group unsubstituted or substituted by a substituent with small steric hindrance, represented by each of $R_2$ and $R_3$, can substantially suppress decomposition caused by transacylation even under alkaline conditions.

In the formula I, $R_2$ may have a structure represented by the following formula II:

(II)

In the formula II, $R_5$ is bound to the nitrogen atom in the terminal amino group, and $R_8$ is bound to the nitrogen atom in the carbamate group. The total number of carbon atoms contained in $R_5$ and $R_8$ is preferably in the range of 1 to 9, more preferably 1 to 5, further preferably 1. The total number of carbon atoms contained in $R_5$ and $R_8$ can be set to the above range to adjust the number of members in the main chain that connects the nitrogen atom in the terminal amino group and the nitrogen atom in the carbamate group, to the preferred range defined above.

$R_5$ is a direct bond or a substituted or unsubstituted 1- to 9-membered alkylene group. The alkylene group is preferably a substituted or unsubstituted $C_1$ to $C_9$ alkylene group, more preferably a substituted or unsubstituted $C_1$ to $C_4$ alkylene group, particularly preferably a substituted or unsubstituted $C_1$ or $C_2$ alkylene group. Alternatively, the alkylene group is preferably an unsubstituted $C_1$ to $C_9$ linear alkylene group, more preferably an unsubstituted $C_1$ to $C_4$ linear alkylene group, particularly preferably an unsubstituted $C_1$ or $C_2$ linear alkylene group. Particularly preferred examples of $R_5$ can include methylene, ethylene, propylene, and butylene. Methylene is preferred.

$R_6$ and $R_7$ are each independently a hydrogen atom, halogen, a hydroxyl group, a substituted or unsubstituted amino group, a nitro group, a cyano group, a carboxyl group, an amide group, or a substituted or unsubstituted monovalent hydrocarbon group optionally containing heteroatom(s). The monovalent hydrocarbon group is preferably 1- to 20-membered, more preferably 1- to 10-membered. Specifically, the monovalent hydrocarbon group is preferably a substituted or unsubstituted $C_1$ to $C_{20}$ alkyl group, $C_2$ to $C_{20}$ alkenyl group, or $C_2$ to $C_{20}$ alkynyl group, a substituted or unsubstituted $C_1$ to $C_{20}$ alkoxyl group, a substituted or unsubstituted $C_3$ to $C_{20}$ cycloalkyl group or $C_3$ to $C_{20}$ heterocyclyl group, a substituted or unsubstituted $C_5$ to $C_{20}$ aryl group, or a substituted or unsubstituted $C_6$ to $C_{20}$ arylalkyl group. One or some carbon atoms in each of these groups may be replaced with 1 or more, preferably 1 to 5, more preferably 1 to 3 heteroatoms. Particularly preferred examples of $R_6$ and $R_7$ can include hydroxymethyl, hydroxyethyl, methyl, ethyl, propyl, methoxymethyl, phenyl, phenylmethyl, tolyl, naphthyl, naphthylmethoxymethyl, and xylyl. Hydroxymethyl, hydroxyethyl, methyl, methoxymethyl, or naphthylmethoxymethyl is preferred.

In consideration of the possible transacylation described above, however, $R_6$ and $R_7$ are each independently preferably a group with small steric hindrance. For example, $R_6$ and $R_7$ are each independently preferably a hydrogen atom or an unsubstituted 1- to 5-membered linear aliphatic hydrocarbon group (e.g., methyl or ethyl). The group with small steric hindrance represented by each of $R_6$ and $R_7$ can substantially suppress decomposition caused by transacylation even under alkaline conditions.

$R_8$ is a direct bond or a substituted or unsubstituted 1- to 5-membered alkylene group. The alkylene group is preferably a substituted or unsubstituted $C_1$ to $C_9$ alkylene group, more preferably a substituted or unsubstituted $C_1$ to $C_4$ alkylene group, particularly preferably a substituted or unsubstituted $C_1$ or $C_2$ alkylene group. Particularly preferred examples of $R_8$ can include a direct bond, methylene, ethylene, propylene, and butylene. A direct bond is preferred.

In the formula II, $R_5$ to $R_8$ may each independently be substituted by one or more of the substituents defined above. In consideration of the possible transacylation described above, however, $R_5$ to $R_8$ are each independently preferably in an unsubstituted form or a form having a substituent with small steric hindrance (unsubstituted 1- to 5-membered linear aliphatic hydrocarbon group, for example, methyl or ethyl), more preferably in an unsubstituted form. The group unsubstituted or substituted by a substituent with small steric hindrance, represented by each of $R_5$ to $R_8$, can substantially suppress decomposition caused by transacylation even under alkaline conditions.

In the formula I, $R_2$ may have a structure represented by the following formula III:

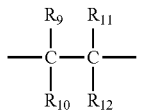
(III)

In the formula III, the carbon atom bound to $R_9$ and $R_{10}$ is bound to the nitrogen atom in the terminal amino group, and the carbon atom bound to $R_{11}$ and $R_{12}$ is bound to the nitrogen atom in the carbamate group.

$R_9$ to $R_{12}$ are each independently a hydrogen atom, halogen, or a substituted or unsubstituted monovalent hydrocarbon group optionally containing heteroatom(s). The monovalent hydrocarbon group is preferably 1- to 10-membered. Specifically, the monovalent hydrocarbon group is preferably a substituted or unsubstituted $C_1$ to $C_{10}$ alkyl group, $C_2$ to $C_{10}$ alkenyl group, or $C_2$ to $C_{10}$ alkynyl group, a substituted or unsubstituted $C_1$ to $C_{10}$ alkoxyl group, a substituted or unsubstituted $C_5$ to $C_{20}$ aryl group, or a substituted or unsubstituted $C_6$ to $C_{20}$ arylalkyl group. One or some carbon atoms in each of these groups may be replaced with one or more, preferably 1 to 5, more preferably 1 to 3 heteroatoms. Particularly preferred examples of $R_9$ to $R_{12}$ can include methyl, ethyl, propyl, methoxymethyl, phenyl, phenylmethyl, tolyl, naphthyl, naphthylmethoxymethyl, and xylyl.

In consideration of the possible transacylation described above, however, $R_9$ to $R_{12}$ are each independently preferably a group with small steric hindrance. For example, $R_9$ to $R_{12}$ are each independently preferably a hydrogen atom or an unsubstituted 1- to 5-membered linear aliphatic hydrocarbon group (e.g., methyl or ethyl). The group with small steric hindrance represented by each of $R_9$ to $R_{12}$ can substantially suppress decomposition caused by transacylation even under alkaline conditions.

Alternatively, $R_9$ or $R_{10}$ and $R_{11}$ or $R_{12}$, together with the carbon atoms to which they are bound, may form a ring optionally containing heteroatom(s). The ring formed by $R_9$ or $R_{10}$ and $R_{11}$ or $R_{12}$ is preferably a substituted or unsubstituted alicyclic group or aromatic group having 3 to 20, preferably 3 to 10 ring members and optionally containing one or more heteroatoms, more preferably alicyclic group having 3 to 6 ring members.

In the formula III, $R_9$ to $R_{12}$ may each independently be substituted by one or more of the substituents defined above. In consideration of the possible transacylation described above, however, $R_9$ to $R_{12}$ are each independently preferably in an unsubstituted form or a form having a substituent with small steric hindrance (unsubstituted 1- to 5-membered linear aliphatic hydrocarbon group, for example, methyl or ethyl), more preferably in an unsubstituted form. The group unsubstituted or substituted by a substituent with small steric hindrance, represented by each of $R_9$ to $R_{12}$, can substantially suppress decomposition caused by transacylation even under alkaline conditions.

More preferably, the aminated oligonucleotide is represented by the formula I, wherein $PG_{1a}$ and $PG_{1b}$ are each independently a hydrogen atom or a protective group for the amino group;
$R_2$ and $R_3$ are each independently a substituted or unsubstituted $C_1$ to $C_{10}$ alkylene group; and
A is an oligonucleotide.

Particularly preferably, the aminated oligonucleotide is represented by the formula I, wherein
$PG_{1a}$ and $PG_{1b}$ are each independently a hydrogen atom or a protective group for the amino group;
$R_2$ is ethylene;
$R_3$ is hexylene; and
A is an oligonucleotide.

Also preferably, the aminated oligonucleotide of the present invention is represented by the following formula Ia:

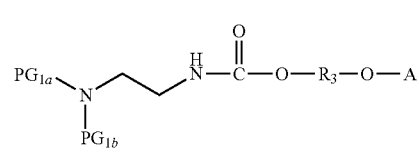
(Ia)

wherein
$PG_{1a}$ and $PG_{1b}$ are each independently a hydrogen atom or a protective group for the amino group, or
$PG_{1a}$ and $PG_{1b}$ together form a protective group for the amino group;
$R_3$ is a divalent group; and
A is an oligonucleotide.

In the formula Ia, A is preferably the oligonucleotide defined in the formula I, and $PG_{1a}$, $PG_{1b}$, and $R_3$ are preferably the groups defined in the formula I.

The present invention also relates to an aminated oligonucleotide probe represented by the formula Ib:

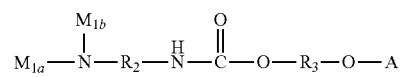
(Ib)

In the formula Ib,
$M_{1a}$ and $M_{1b}$ are each independently a hydrogen atom or a group derived from a probe molecule, or
$M_{1a}$ and $M_{1b}$ together form a group derived from a probe molecule;
$R_2$ and $R_3$ are each independently a divalent group, or
$R_2$ and $R_3$, together with the carbamate group to which they are bound, form a ring; and
A is an oligonucleotide.

In the formula Ib, A is preferably the oligonucleotide defined in the formula I, and $R_2$ and $R_3$ are preferably the groups defined in the formula I.

The group derived from a probe molecule, represented by each of $M_{1a}$ and $M_{1b}$, is preferably a group bound to the terminal amino group of the amino linker moiety so that the probe molecule defined above can form at least one covalent bond with the terminal amino group. Specifically, $M_{1a}$ is preferably a hydrogen atom, and $M_{1b}$ is preferably a group derived from a probe molecule selected from the group consisting of biotin, PEG, CyDye (e.g., Cy3 and Cy5), FITC, RITC, rhodamine, Texas Red, TET, TAMRA, FAM, HEX, ROX, ferrocene, Nile Blue, and GFP.

The aminated oligonucleotide represented by the formula I or Ia or the aminated oligonucleotide probe represented by the formula Ib according to the present invention may be in the form of a salt or a solvate. In the present specification, the "aminated oligonucleotide represented by the formula I", the "aminated oligonucleotide represented by the formula Ia", or the "aminated oligonucleotide probe represented by the formula Ib" means not only the compound itself but salts or solvates thereof. The salt of the aminated oligonucleotide represented by the formula I or Ia or the aminated oligonucleotide probe represented by the formula Ib is not limited and is preferably, for example, a salt with an inorganic or organic acid such as hydrochloric acid, phosphoric acid, nitric acid, sulfuric acid, carbonic acid, perchloric acid, formic acid, acetic acid, maleic acid, fumaric acid, or benzoic acid, or a triethylammonium ion, a sodium ion, or a potassium ion.

Use of the aminated oligonucleotide represented by the formula I or Ia in a form as described above can further improve stability under alkaline conditions and produce an aminated oligonucleotide more highly reactive with a probe molecule, compared with the aminated oligonucleotide probe of the conventional technique. This feature allows the aminated oligonucleotide probe represented by the formula Ib to be produced at high yields and low cost.

<2. Solid-Phase Carrier for Use in Synthesis of Aminated Oligonucleotide>

The present invention also relates to a solid-phase carrier represented by the formula IV:

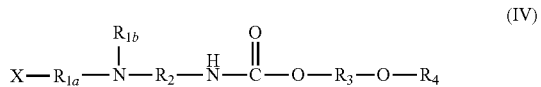

or a solid-phase carrier represented by the formula V:

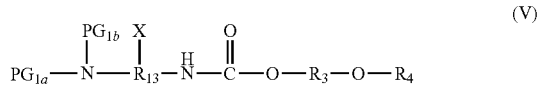

The present inventors have found that use of the solid-phase carrier represented by the formula IV or V as a carrier for solid-phase oligonucleotide synthesis can synthesize, at high yields, the aminated oligonucleotide of interest represented by the formula I or Ia substantially without the decomposition of the amino linker moiety even by the excision of the aminated oligonucleotide from a carrier material and the base deprotection treatment under alkaline conditions in the final step of the solid-phase synthesis as in the phosphoramidite method.

In the formulas IV and V, $PG_{1a}$, $PG_{1b}$, $R_2$, and $R_3$ are as defined above.

In the formulas IV and V, X is a carrier material. X is not particularly limited as long as its surface can form a covalent bond with the terminal functional groups of $R_{1a}$ and $R_{1b}$ or $R_{13}$ described below. A carrier material routinely used in the art can be used. Preferred examples of the carrier material can include, but not limited to, glass (e.g., porous spherical glass (Controlled Pore Glass: CPG), quartz glass, borosilicate glass, and soda lime glass), silicon, fiber, wood, paper, ceramics, and plastics (e.g., polystyrene resin, polyester resin, polyethylene resin, polypropylene resin, acrylonitrile butadiene styrene resin (ABS resin), nylon resin, acrylic resin, fluororesin, polycarbonate resin, polyurethane resin, methylpentene resin, phenol resin, melamine resin, epoxy resin, and vinyl chloride resin). Glass, silicon, a ceramic, or a plastic is preferably used. Use of the carrier material can immobilize thereon the amino linker moiety for oligonucleotide binding.

In the formula IV, the bond between X and $R_{1a}$ may be a bond cleavable under conditions for cleaving the bond between $R_{1a}$ and the terminal amino group of the amino linker moiety. Alternatively, the bond between X and $R_{1a}$ may be a bond that is maintained without being cleaved under the conditions. In the latter case, the bond between $R_{1a}$ and the terminal amino group of the amino linker moiety is cleaved to excise the aminated oligonucleotide of the present invention from the carrier material having the structure X—$R_{1a}$. In this case, the bond between X and $R_{1a}$ is not particularly limited as long as the bond satisfies the conditions.

When the bond between X and $R_{1a}$ in the formula IV is a bond cleavable under conditions for cleaving the bond between $R_{1a}$ and the terminal amino group of the amino linker moiety and in the case of the formula V, the surface of the carrier material preferably has a functional group capable of forming, with $R_{1a}$, a bond cleavable by the excision treatment of the aminated oligonucleotide from the carrier material under alkaline conditions in solid-phase oligonucleotide synthesis. Preferred examples of the functional group can include, but not limited to, an amino group, a carboxyl group, an aldehyde group, a ketone group, a halogenated alkyl group, and a sulfonyl chloride group. Use of the carrier material having any of these functional groups allows the solid-phase carrier of the present invention to be used in solid-phase oligonucleotide synthesis routinely used in the art.

In the formula IV, $R_{1a}$ is a direct bond or a divalent group. When $R_{1a}$ is a divalent group and the bond between X and $R_{1a}$ is maintained without being cleaved under conditions for cleaving the bond between $R_{1a}$ and the terminal amino group of the amino linker moiety, $R_{1a}$ is not particularly limited as long as $R_{1a}$ is a divalent group that allows the bond between X and $R_{1a}$ to satisfy the conditions. When the bond between X and $R_{1a}$ is cleavable under conditions for cleaving the bond between $R_{1a}$ and the terminal amino group of the amino linker moiety, $R_{1a}$ is not particularly limited as long as the divalent group has a bond that is formed by at least 2 functional groups between the functional group present on the surface of X and the terminal amino group of the amino linker moiety and is cleavable under the conditions. The functional groups are preferably functional groups capable of forming a bond cleavable by the excision treatment of the aminated oligonucleotide from the carrier material under alkaline conditions in solid-phase oligonucleotide synthesis. Preferred examples of the functional groups can include, but not limited to, an amino group, a carboxyl group, an aldehyde group, and a ketone group. Use of the divalent group having a bond formed by the functional groups allows the solid-phase carrier of the present invention to be used in solid-phase oligonucleotide synthesis routinely used in the art.

$R_{1a}$ is preferably a substituted or unsubstituted divalent hydrocarbon group optionally containing heteroatom(s) and having a bond formed by at least 2 functional groups selected from the group consisting of an amino group, a carboxyl group, an aldehyde group, and a ketone group. In this case, $R_{1a}$ forms a covalent bond by 2 functional groups selected from these functional groups between the functional group present on the surface of X and the terminal amino group of the amino linker moiety. Preferred examples of the divalent hydrocarbon group can include, but not limited to, a 1- to 10-, preferably 1- to 5-, more preferably 2-membered substituted or unsubstituted divalent aliphatic hydrocarbon group, a substituted or unsubstituted divalent alicyclic group having 3 to 20 ring members, and a substituted or unsubstituted divalent aromatic group having 5 to 20 ring members, wherein these groups each have the covalent bond formed by at least 2 functional groups. These groups may each contain one or more heteroatoms. Particularly preferred examples of $R_{1a}$ can include a divalent group derived from succinic acid, citric acid, squaric acid, or benzene-1,2,4-tricarboxylic anhydride (trimellitic anhydride).

$R_{1b}$ is a hydrogen atom.

Alternatively, $R_{1a}$ and $R_{1b}$ may together form a group bound to X and the amino group. When the bond between X and $R_{1a}$ is maintained without being cleaved under conditions for cleaving the bond of $R_{1a}$ and $R_{1b}$ with the terminal amino group of the amino linker moiety, $R_{1a}$ and $R_{1b}$ are not particularly limited as long as the group formed by $R_{1a}$ and $R_{1b}$ allows the bond between X and $R_{1a}$ to satisfy the conditions. When the bond between X and $R_{1a}$ is cleavable under conditions for cleaving the bond of $R_{1a}$ and $R_{1b}$ with the terminal amino group of the amino linker moiety, $R_{1a}$ and $R_{1b}$ are not particularly limited as long as the group formed by $R_{1a}$ and $R_{1b}$ has a bond that is formed by at least 3 functional groups between the functional group present on the surface of X and the terminal amino group of the amino linker moiety and is cleavable under the conditions. The functional groups are selected from among the examples defined in $R_{1a}$ and are preferably functional groups capable of forming a bond cleavable by the excision treatment of the aminated oligonucleotide from the carrier material under alkaline conditions in solid-phase oligonucleotide synthesis. Use of the group having a bond formed by the functional groups allows the solid-phase carrier of the present invention to be used in solid-phase oligonucleotide synthesis routinely used in the art.

$R_{1a}$ and $R_{1b}$ are preferably a substituted or unsubstituted hydrocarbon group optionally containing heteroatom(s) and having a bond formed by at least 3 functional groups selected from the group consisting of an amino group, a carboxyl group, an aldehyde group, and a ketone group. In this case, the group formed by $R_{1a}$ and $R_{1b}$ forms a covalent bond by 3 functional groups selected from these functional groups between the functional group present on the surface of X and the terminal amino group of the amino linker moiety. Preferred examples of the hydrocarbon group can include, but not limited to, a 1- to 10-, preferably 1- to 5-membered substituted or unsubstituted aliphatic hydrocarbon group, a substituted or unsubstituted alicyclic group having 3 to 20 ring members, and a substituted or unsubstituted aromatic group having 5 to 20 ring members, wherein these groups each have the covalent bond formed by at least 3 functional groups. These groups may each contain one or more heteroatoms. Particularly preferred examples of $R_{1a}$ and $R_{1b}$ can include a group derived from benzene-1,2,4-tricarboxylic anhydride (trimellitic anhydride).

In the formula V, $R_{13}$ is a trivalent group. $R_{13}$ is not particularly limited as long as has $R_{13}$ has a bond formed by at least one functional group with the functional group present on the surface of X and does not inhibit binding ability against a solid and the complementary binding between the oligonucleotide and a target oligonucleotide. The functional group is selected from among the examples defined in $R_{1a}$ and is preferably a functional group capable of forming a bond cleavable by the excision treatment of the aminated oligonucleotide from the carrier material under alkaline conditions in solid-phase oligonucleotide synthesis. Use of the trivalent group having a bond formed by the functional group allows the solid-phase carrier of the present invention to be used in solid-phase oligonucleotide synthesis routinely used in the art.

$R_{13}$ is preferably a substituted or unsubstituted trivalent hydrocarbon group optionally containing heteroatom(s) and having a bond formed by at least one functional group selected from the group consisting of an amino group, a carboxyl group, a hydroxy group, an aldehyde group, and a ketone group. In this case, the trivalent hydrocarbon group forms a covalent bond by one functional group selected from these functional groups with the functional group present on the surface of X. Preferred examples of the trivalent hydrocarbon group can include, but not limited to, a 1- to 10-, preferably 1- to 5-membered substituted or unsubstituted trivalent aliphatic hydrocarbon group, a substituted or unsubstituted trivalent alicyclic group having 3 to 20 ring members, and a substituted or unsubstituted trivalent aromatic group having 5 to 20 ring members, wherein these groups each has the covalent bond formed by at least one functional group. These groups may each contain one or more heteroatoms. Particularly preferred examples of $R_{13}$ can include a 3- or 4-membered aliphatic hydrocarbon-derived trivalent group having the covalent bond formed by at least one functional group. In the trivalent aromatic group represented by $R_{13}$, the length of the main chain is determined depending on the number of ring atoms in the aromatic group. This may increase the distance between the carbamate group and the amino group, thereby reducing the reactivity of the amino group. Hence, the aliphatic hydrocarbon group represented by $R_{13}$ can keep the distance between the carbamate group and the amino group within a fixed range, thereby improving the reactivity of the amino group.

Alternatively, $R_{13}$ and $R_3$, together with the carbamate group to which they are bound, may form a ring. The ring formed by $R_{13}$ and $R_3$ is preferably a substituted or unsubstituted alicyclic group or aromatic group having 5 to 10, preferably 5 or 6 ring members and optionally containing one or more heteroatoms, more preferably 4,5-dihydrooxazol-2(3H)-one-4,5-diyl. In this case, a preferred combination is $R_{13}$ having 1 to 10, preferably 1 to 5, more preferably 2 members in the main chain and $R_3$ having 1 to 10, preferably 2 to 6, more preferably 2 members in the main chain.

$R_4$ is a protective group for the hydroxy group. A hydrophobic protective group that is deprotected under acidic conditions is preferred. Preferred examples of the protective group can include, but not limited to, a trityl group, a monosubstituted or disubstituted trityl group, a pyranyl group, a furanyl group, an o-nitrobenzyl group, and a levulinyl group. A trityl group or a monosubstituted or disubstituted trityl group is preferred. Examples of the substituent(s) for the trityl group in the substituted trityl group can include alkoxyl groups having 1 to 4 carbon atoms. The monosubstituted or disubstituted trityl group is preferably a monomethoxytrityl group, a monoethoxytrityl group, a monopropoxytrityl group, a monoisopropoxytrityl group, a monobutoxytrityl group, a dimethoxytrityl group, a diethoxytrityl group, a dipropoxytrityl group, a diisopropoxytrityl group, or a dibutoxytrityl group. Use of the protective group that is deprotected under acidic conditions can deprotect the hydroxy group without excising the carrier material.

Preferably, the solid-phase carrier is represented by the formula IV, wherein
X is a carrier material selected from glass and plastics;
$R_{1a}$ is a direct bond, and
$R_{1b}$ is a hydrogen atom, or
$R_{1a}$ and $R_{1b}$ together form a 1- to 10-membered substituted or unsubstituted aliphatic hydrocarbon group, a substituted or unsubstituted alicyclic group having 3 to 20 ring members, or a substituted or unsubstituted aromatic group having 5 to 20 ring members, bound to X and the amino group;
$R_2$ and $R_3$ are each independently a substituted or unsubstituted $C_1$ to $C_{10}$ alkylene group; and
$R_4$ is a trityl group or a monosubstituted or disubstituted trityl group.

More preferably, the solid-phase carrier is represented by the formula IV, wherein
X is CPG or polystyrene resin having an amino group;
$R_{1a}$ and $R_{1b}$ together form imide or amide of benzene-1,2,4-tricarboxylic acid having amide formed with the amino group in X and imide or amide formed with the amino group bound to $R_2$;
$R_2$ is ethylene;
$R_3$ is hexylene; and
$R_4$ is a trityl group or a monosubstituted or disubstituted trityl group.

Also preferably, the solid-phase carrier is represented by the formula V, wherein
X is a carrier material selected from glass and plastics;
$R_{13}$ is a 1- to 10-membered substituted or unsubstituted trivalent aliphatic hydrocarbon group;
$R_3$ is a substituted or unsubstituted $C_1$ to $C_{10}$ alkylene group; and
$R_4$ is a trityl group or a monosubstituted or disubstituted trityl group.

More preferably, the solid-phase carrier is represented by the formula V, wherein
X is CPG or polystyrene resin having an amino group;
$R_{13}$ is substituted ethylene having a bond formed with X by one functional group selected from the group consisting of an amino group, a carboxyl group, a hydroxy group, an aldehyde group, and a ketone group;
$R_3$ is hexylene; and
$R_4$ is a trityl group or a monosubstituted or disubstituted trityl group.

Also, the solid-phase carrier of the present invention is preferably represented by the following formula IVa:

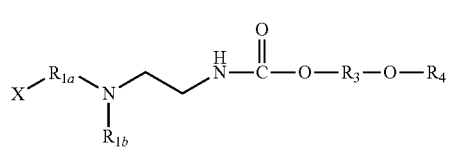

(IVa)

wherein
X is a carrier material;
$R_{1a}$ is a direct bond or a divalent group, and
$R_{1b}$ is a hydrogen atom, or
$R_{1a}$ and $R_{1b}$ together form a group bound to X and the amino group;
$R_3$ is a divalent group; and
$R_4$ is a protective group for the hydroxy group.

In the formula IVa, X is preferably the carrier material defined in the formula IV; $R_3$ is preferably the group defined in the formula I; and $R_{1a}$, $R_{1b}$, and $R_4$ are preferably the groups defined in the formula IV.

The solid-phase carrier represented by the formula IV, V, or IVa of the present invention may be in the form of a salt or a solvate. In the present specification, the "solid-phase carrier represented by the formula IV", the "solid-phase carrier represented by the formula V", or the "solid-phase carrier represented by the formula IVa" means not only the compound itself but salts or solvates thereof. The salt of the solid-phase carrier represented by the formula IV, V, or IVa is not limited and is preferably, for example, a salt with an inorganic or organic acid such as hydrochloric acid, phosphoric acid, nitric acid, sulfuric acid, carbonic acid, perchloric acid, formic acid, acetic acid, maleic acid, fumaric acid, or benzoic acid, or a triethylammonium ion, a sodium ion, or a potassium ion.

Use of the solid-phase carrier represented by the formula IV, V, or IVa in a form as described above can further improve stability under alkaline conditions, compared with the solid-phase carrier for solid-phase oligonucleotide synthesis of the conventional technique.

<3. Methods for Producing Solid-Phase Carrier and Aminated Oligonucleotide>

The aminated oligonucleotide represented by the formula I and the solid-phase carrier represented by the formula IV according to the present invention can each be produced using an amino linker compound represented by the formula X:

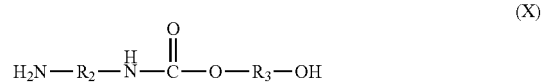

(X)

wherein $R_2$ and $R_3$ are as defined above in the formulas I and IV,
as a synthetic intermediate.

The amino linker compound represented by the formula X can be produced by a method comprising the following steps:

(A) reacting a diol represented by the formula VI:

(VI)

wherein $R_3$ is as defined above,
with a carbonyl derivative represented by the formula VII:

(VII)

wherein $L_1$ and $L_2$ are each independently a hydrogen atom or a leaving group, to form a compound represented by the formula VIII:

(VIII)

wherein $L_1$ and $R_3$ are as defined above; and (B) reacting the compound represented by the formula VIII with a diamine represented by the formula IX:

(IX)

wherein $R_2$ is as defined above,
to form an amino linker compound represented by the formula X:

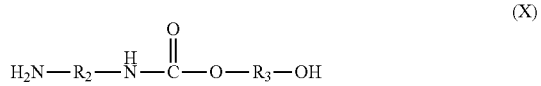

wherein $R_2$ and $R_3$ are as defined above.

In this context, $L_1$ and $L_2$ are not particularly limited as long as each of these groups is a leaving group that is used in the art for forming an ester bond through reaction with a hydroxy group. Preferred examples of the leaving group can include, but not limited to, an imidazolyl group, a chloro group, a trichloromethoxy group, and a 1,2,4-triazolyl group. $L_1$ and $L_2$ may be the same or different.

The esterification reaction in the step A and the amidation reaction in the step B can both be carried out under usual reaction conditions routinely used in the art.

Also, the solid-phase carrier represented by the formula IV can be produced by a method comprising the following step:

(C) reacting the amino linker compound represented by the formula X with a precursor compound of $R_{1a}$ and $R_{1b}$ and a precursor material of X to form the solid-phase carrier represented by the formula IV.

In this context, the precursor compound of $R_{1a}$ and $R_{1b}$ means a compound that has a functional group capable of forming a bond between the functional group present on the surface of X and the terminal amino group of the amino linker moiety as described above, or an activated group thereof, and is capable of forming $R_{1a}$ and $R_{1b}$ through reaction with the precursor material of X and the amino linker compound represented by the formula X. The precursor material of X means a carrier material that has a functional group capable of forming a bond with the functional group or the activated group thereof in the precursor compound of $R_{1a}$ and $R_{1b}$, or an activated group thereof, and is capable of forming X through reaction with the precursor compound of $R_{1a}$ and $R_{1b}$ or with the reaction product of the precursor compound of $R_{1a}$ and $R_{1b}$ and the amino linker compound represented by the formula X.

The reaction in the step C can be carried out under usual reaction conditions routinely used in the art.

The step C may be carried out using the amino linker compound, sequentially from the production of the amino linker compound represented by the formula X by the method comprising the steps A and B. Alternatively, the step C may be carried out independently using the preliminarily prepared amino linker compound represented by the formula X.

After the production of the solid-phase carrier represented by the formula IV, an oligonucleotide can be synthesized according to solid-phase synthesis routinely used in the art to obtain the aminated oligonucleotide represented by the formula I.

In this way, the aminated oligonucleotide or the solid-phase carrier of the present invention can be produced.

EXAMPLES

Hereinafter, the present invention will be described further specifically with reference to Examples. However, the technical scope of the present invention is not limited by these Examples.

Synthesis Example 1

Synthesis of Solid-Phase Carrier for 3' Amination Modification

[Material and Method]

Thin-layer chromatography was performed on a Silica gel 60F$_{254}$ plate (Merck KGaA). Column chromatography was performed using Wakogel C-200 (Wako Pure Chemical Industries, Ltd.), Silica Gel 60 (Nacalai Tesque, Inc.), or Wakogel 100 C18 (reverse-phase; Wako Pure Chemical Industries, Ltd.). $^1$H NMR (270 MHz) and $^{13}$C NMR (67.8 MHz) were measured using dimethyl sulfoxide-d$_6$ as a solvent, tetramethylsilane as an internal standard, and JEOL JNM-EX270.

[Summary of Synthesis]

A solid-phase carrier for 3' amination modification was synthesized according to the following scheme 1:

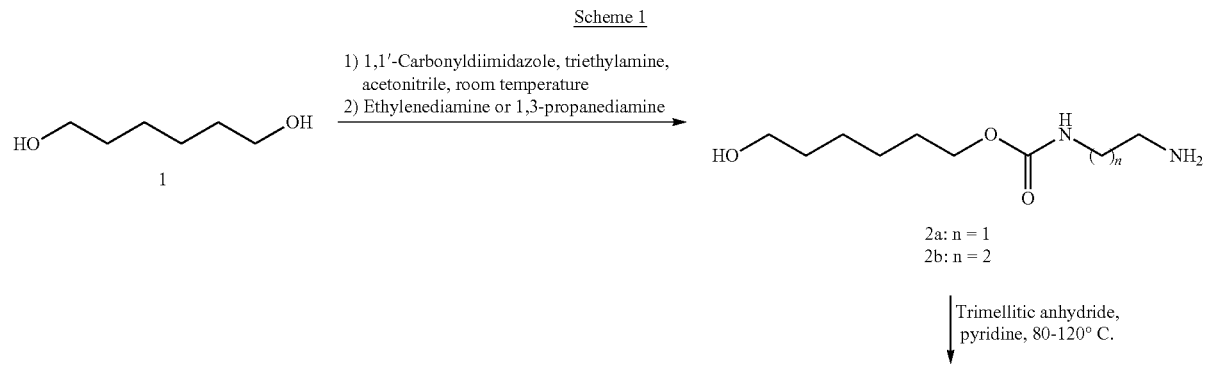

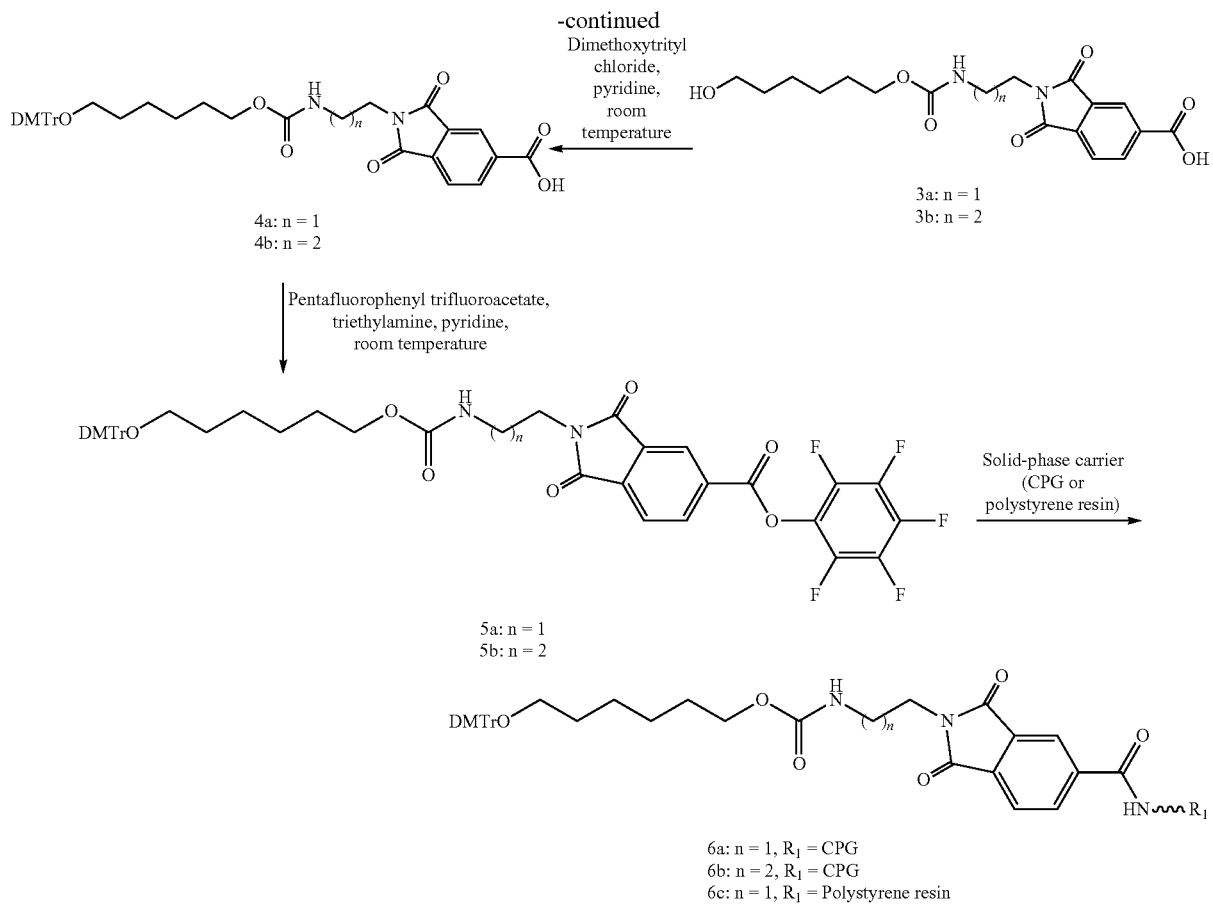

6a: n = 1, R₁ = CPG
6b: n = 2, R₁ = CPG
6c: n = 1, R₁ = Polystyrene resin

Example 1

Synthesis of revH Linker-CPG Solid-Phase Carrier (Compound 6a)

1-[(2-Aminoethyl)aminocarbonyl]oxy-6-hexanol (compound 2a)

In an argon atmosphere, 590 mg (5.00 mmol) of 1,6-hexanediol (compound 1) was dissolved in 20 ml of acetonitrile. To the solution, 0.42 ml (3.00 mmol) of triethylamine and 324 mg (2.00 mmol) of 1,1′-carbonyldiimidazole were added, and the mixture was stirred at room temperature for 1.5 hours. Subsequently, 0.33 ml (5.00 mmol) of ethylenediamine was added to the reaction solution, and the mixture was stirred at room temperature for 2 hours. The reaction solution was concentrated under reduced pressure, followed by azeotropy of the residue with ethanol (10 ml×3). The residue was dissolved in 15 ml of water. The solution was purified by reverse-phase silica gel column chromatography (elution solvent: acetonitrile-water) to obtain 270 mg (yield: 75%) of the title compound (compound 2a) as a white solid.

ESI-MS Calculated: 205.1547 ($C_9H_{21}N_2O_3$ [M+H]⁺). Found: 205.1544. ¹H NMR (270 MHz, DMSO-$d_6$) δ: 6.98 (br t, 1H, NH, J=5.9 Hz), 3.91 (t, 2H, CH₂, J=6.6 Hz), 3.37 (t, 2H, CH₂, J=6.5 Hz), 2.95 (dt, 2H, CH₂, J=5.9, 6.6 Hz), 2.53 (t, 2H, CH₂, J=6.6 Hz), 1.52 (m, 2H, CH₂), 1.40 (m, 2H, CH₂), 1.34-1.26 (m, 4H, CH₂×2); ¹³C NMR (67.8 MHz, DMSO-$d_6$) δ: 156.42 (C), 63.52 (CH₂), 60.56 (CH₂), 43.95 (CH₂), 41.55 (CH₂), 32.39 (CH₂), 28.72 (CH₂), 25.26 (CH₂), 25.16 (CH₂).

1-[(4-Carboxyphthalimidylethyl)aminocarbonyl]oxy-6-hexanol (compound 3a)

In an argon atmosphere, 670 mg (3.30 mmol) of 1-[(2-aminoethyl)aminocarbonyl]oxy-6-hexanol (compound 2a) and 576 mg (3.00 mmol) of trimellitic anhydride were dissolved in 25 ml of pyridine, and the solution was heated to reflux at 80° C. for 1 hour and further at 120° C. for 18 hours. The reaction solution was cooled to room temperature and then concentrated under reduced pressure. The residue was subjected to azeotropy with ethanol (5 ml×3). The remaining white substance was suspended in 20 ml of ethyl acetate. The precipitate was collected by filtration from the suspension to obtain 1.10 g (88%) of the title compound (compound 3a) as a white powder.

ESI-MS Calculated: 377.1354 ($C_{18}H_{21}N_2O_7$ [M−H]⁻). Found: 377.1358. ¹H NMR (DMSO-$d_6$) δ: 8.35 (dd, 1H, Phth, J=1.3, 7.9 Hz), 8.22 (s, 1H, Phth), 7.98 (d, 1H, Phth, J=7.9 Hz), 7.18 (t, 1H, NH, J=6.1 Hz), 3.85 (t, 2H, CH₂, J=6.5 Hz), 3.66 (t, 2H, CH₂, J=5.4 Hz), 3.37 (t, 2H, CH₂, J=6.4 Hz), 3.24 (dt, 2H, CH₂, J=5.3, 6.1 Hz), 1.46-1.34 (m, 4H, CH₂×2), 1.26-1.21 (m, 4H, CH₂×2); ¹³C NMR (DMSO-$d_6$) δ: 167.17 (C), 167.14 (C), 165.83 (C), 156.47 (C), 136.25 (C), 135.07 (CH), 132.24 (C), 123.23 (CH), 122.83 (CH), 63.66 (CH₂), 60.59 (CH₂), 38.28 (CH₂), 38.01 (CH₂), 32.41 (CH₂), 28.64 (CH₂), 25.14 (CH₂).

1-[(4-Carboxyphthalimidylethyl)aminocarbonyl]oxy-O-(dimethoxytrityl)-6-hexanol (compound 4a)

In an argon atmosphere, 1.02 g (2.70 mmol) of 1-[(4-carboxyphthalimidylethyl)aminocarbonyl]oxy-6-hexanol (compound 3a) was dissolved in 27 ml of pyridine. To the solution, 915 mg (2.70 mmol) of dimethoxytrityl chloride was added, and the mixture was stirred at room temperature. After 2 hours, 440 mg (1.30 mmol) of dimethoxytrityl chloride was further added to the reaction solution, and the mixture was stirred at room temperature for additional 2 hours. 5 ml of ethanol was added to the reaction solution, and the mixture was then concentrated under reduced pressure. The residue was dissolved in 150 ml of chloroform. The solution was washed with 50 ml of water twice and 50 ml of saturated saline once and dried over sodium sulfate. The solution was concentrated under reduced pressure, followed by azeotropy with 5 ml of toluene. The residue was purified by silica gel column chromatography (elution solvent: ethanol-chloroform, containing 0.3% pyridine) to obtain 1.88 g (pyridine salt, yield: 92%) of the title compound (compound 4a) as a yellow foam.

ESI-MS Calculated: 679.2661 ($C_{39}H_{39}N_2O_9$ [M−H]$^-$). Found: 679.2673. $^1$H NMR (DMSO-$d_6$) δ: 8.58 (m, 2H, Py), 8.34 (dd, 1H, Phth, J=1.3, 7.6 Hz), 8.22 (s, 1H, Phth), 7.96 (d, 1H, Phth, J=7.6 Hz), 7.78 (m, 1H, Py), 7.38 (m, 2H, Py), 7.36-7.17 (m, 10H, DMT, NH), 6.87 (d, 4H, DMT, J=8.9 Hz), 3.83 (t, 2H, $CH_2$, J=6.6 Hz), 3.73 (s, 6H, $OCH_3$×2), 3.66 (t, 2H, $CH_2$, J=5.6 Hz), 3.24 (m, 2H, $CH_2$), 2.95 (t, 2H, $CH_2$, J=6.4 Hz), 1.52 (m, 2H, $CH_2$), 1.43 (m, 2H, $CH_2$), 1.34-1.16 (m, 4H, $CH_2$×2); $^{13}$C NMR (DMSO-$d_6$) δ: 167.08 (C), 165.76 (C), 157.87 (C), 156.39 (C), 149.51 (CH, Py), 145.18 (C), 136.10 (CH, Py), 136.00 (C), 135.05 (CH), 134.97 (C), 132.20 (C), 129.48 (CH), 127.66 (CH), 127.57 (CH), 126.43 (CH), 123.80 (CH, Py), 123.13 (CH), 122.78 (CH), 113.02 (CH), 85.07 (C), 63.55 ($CH_2$), 62.59 ($CH_2$), 54.90 ($CH_3$), 38.25 ($CH_2$), 37.95 ($CH_2$), 29.30 ($CH_2$), 28.47 ($CH_2$), 25.36 ($CH_2$), 25.02 ($CH_2$).

1-[(4-Pentafluorophenoxycarbonylphthalimidylethyl)aminocarbonyl]oxy-O-(dimethoxytrityl)-6-hexanol (compound 5a)

In an argon atmosphere, 380 mg (0.50 mmol) of 1-[(4-carboxyphthalimidylethyl)aminocarbonyl]oxy-O-(dimethoxytrityl)-6-hexanol (compound 4a, pyridine salt) was dissolved in 8 ml of pyridine. To the solution, 0.17 ml (1.00 mmol) of pentafluorophenyl trifluoroacetate and 0.28 ml (2.00 mmol) of triethylamine were added, and the mixture was stirred at room temperature for 2 hours. The reaction solution was concentrated under reduced pressure. Then, the residue was dissolved in 80 ml of ethyl acetate. The solution was washed with 50 ml of water once, 50 ml of a saturated aqueous solution of sodium bicarbonate once, 50 ml of water once, and 50 ml of saturated saline once and dried over sodium sulfate. The solution was concentrated under reduced pressure, followed by azeotropy with 5 ml of toluene. The residue was purified by silica gel column chromatography (elution solvent: ethyl acetate-hexane, containing 0.3% pyridine) to obtain 375 mg (yield: 89%) of the title compound (compound 5a) as a yellow foam.

ESI-MS Calculated: 869.2468 ($C_{45}H_{39}F_5N_2O_9Na$ [M+Na]$^+$). Found: 869.2470. $^1$H NMR (DMSO-$d_6$) δ: 8.57 (dd, 1H, Phth, J=1.3, 7.9 Hz), 8.46 (s, 1H, Phth), 8.12 (d, 1H, Phth, J=7.9 Hz), 7.38-7.18 (m, 10H, DMT, NH), 6.87 (d, 4H, DMT, J=8.6 Hz), 3.83 (t, 2H, $CH_2$, J=6.6 Hz), 3.72 (s, 6H, $OCH_3$×2), 3.69 (m, 2H, $CH_2$), 3.26 (m, 2H, $CH_2$), 2.95 (t, 2H, $CH_2$, J=6.4 Hz), 1.52 (m, 2H, $CH_2$), 1.42 (m, 2H, $CH_2$), 1.32-1.18 (m, 4H, $CH_2$×2).

revH Linker-CPG Solid-Phase Carrier (Compound 6a)

In a glass vial, 84.7 mg (0.10 mmol) of 1-[(4-pentafluorophenoxycarbonylphthalimidylethyl)aminocarbonyl]oxy-O-(dimethoxytrityl)-6-hexanol (compound 5a) was dissolved in 5 ml of a mixed solution of pyridine and triethylamine (9:1). To the solution, 220 mg (25 μmol) of LCAA-CPG was added, and the mixture was vigorously shaken at room temperature for 24 hours. The CPG was washed with pyridine (5 ml×4) and methylene chloride (10 ml×2) and then dried under reduced pressure at room temperature for 1.5 hours. Subsequently, 5 ml of a capping solution (mixed solution of pyridine and acetic anhydride (9:1) containing 0.1 M dimethylaminopyridine) was added to the CPG, and the mixture was vigorously shaken at room temperature for 2 hours. The CPG was washed with pyridine (5 ml×4) and methylene chloride (10 ml×2) and then dried under reduced pressure at room temperature to obtain the title compound (compound 6a) (34.8 μmol/g).

Example 2

Synthesis of revPro Linker-CPG Solid-Phase Carrier (Compound 6b)

1-[(3-Aminopropyl)aminocarbonyl]oxy-6-hexanol (compound 2b)

859 mg (yield: 65%) of the title compound (compound 2b) was obtained as a white solid by the same treatment as in the synthesis of compound 2a using 1.77 g (15.0 mmol) of 1,6-hexanediol (compound 1) as a starting material and 1.25 ml (15.0 mmol) of 1,3-propanediamine instead of ethylenediamine.

ESI-MS Calculated: 219.1703 ($C_{10}H_{23}N_2O_3$ [M+H]$^+$). Found: 219.1701. $^1$H NMR (270 MHz, DMSO-$d_6$) δ: 7.04 (br t, 1H, NH), 3.91 (t, 2H, $CH_2$, J=6.6 Hz), 3.38 (t, 2H, $CH_2$, J=6.5 Hz), 3.00 (q, 2H, $CH_2$, J=6.3 Hz), 2.53 (t, 2H, $CH_2$, J=6.6 Hz), 1.54-1.38 (m, 6H, $CH_2$×3), 1.34-1.26 (m, 4H, $CH_2$×2); $^{13}$C NMR (67.8 MHz, DMSO-$d_6$) δ: 156.35 (C), 63.48 ($CH_2$), 60.58 ($CH_2$), 38.86 ($CH_2$), 37.89 ($CH_2$), 33.03 ($CH_2$), 32.42 ($CH_2$), 28.75 ($CH_2$), 25.27 ($CH_2$), 25.17 ($CH_2$).

1-[(4-Carboxyphthalimidylpropyl)aminocarbonyl]oxy-6-hexanol (compound 3b)

949 mg (yield: 81%) of the title compound (compound 3b) was obtained as a white solid by the same treatment as in the synthesis of compound 3a using 655 mg (3.00 mmol) of 1-[(3-aminopropyl)aminocarbonyl]oxy-6-hexanol (compound 2b) as a starting material.

ESI-MS Calculated: 391.1511 ($C_{19}H_{23}N_2O_7$ [M−H]$^-$). Found: 391.1514. $^1$H NMR (DMSO-$d_6$) δ: 13.69 (br s, 1H, COOH), 8.35 (dd, 1H, Phth, J=1.6, 7.6 Hz), 8.21 (m, 1H, Phth), 7.98 (d, 1H, Phth, J=7.6 Hz), 7.08 (br t, 1H, NH, J=5.3 Hz), 3.89 (t, 2H, $CH_2$, J=6.6 Hz), 3.59 (t, 2H, $CH_2$, J=7.3 Hz), 3.37 (t, 2H, $CH_2$, J=6.3 Hz), 3.01 (dt, 2H, $CH_2$, J=5.3, 7.2 Hz), 1.75 (m, 2H, $CH_2$), 1.50 (m, 2H, $CH_2$), 1.40 (m, 2H, $CH_2$), 1.28 (m, 4H, $CH_2$×2); $^{13}$C NMR (DMSO-$d_6$) δ: 167.10 (C), 167.08 (C), 165.79 (C), 156.30 (C), 136.15 (C), 135.14 (CH), 134.98 (C), 132.12 (CH), 123.30 (CH), 122.91

(CH), 63.60 (CH$_2$), 60.58 (CH$_2$), 37.97 (CH$_2$), 35.65 (CH$_2$), 28.69 (CH$_2$), 28.23 (CH$_2$), 25.24 (CH$_2$), 25.17 (CH$_2$).

1-[(4-Carboxyphthalimidylpropyl)aminocarbonyl]oxy-O-(dimethoxytrityl)-6-hexanol (compound 4b)

1.14 g (yield: 86%) of the title compound (compound 4b, pyridine salt) was obtained as a yellow foam by the same treatment as in the synthesis of compound 4a using 643 mg (1.70 mmol) of 1-[(4-carboxyphthalimidylpropyl)aminocarbonyl]oxy-6-hexanol (compound 3b) as a starting material.

ESI-MS Calculated: 693.2818 (C$_{40}$R$_{41}$N$_2$O$_9$ [M−H]$^-$). Found: 693.2821. $^1$H NMR (DMSO-d$_6$) δ: 8.58 (m, 2H, Py), 8.35 (d, 1H, Phth, J=7.6 Hz), 8.21 (s, 1H, Phth), 7.97 (d, 1H, Phth, J=7.6 Hz), 7.79 (m, 1H, Py), 7.38 (m, 2H, Py), 7.35-7.21 (m, 9H, DMT), 7.08 (br t, 1H, NH), 6.88 (d, 4H, DMT, J=8.9 Hz), 3.87 (t, 2H, CH$_2$, J=6.6 Hz), 3.73 (s, 6H, OCH$_3$×2), 3.59 (t, 2H, CH$_2$, J=6.9 Hz), 3.01 (q, 2H, CH$_2$, J=6.0 Hz), 2.94 (t, 2H, CH$_2$, J=6.3 Hz), 1.74 (m, 2H, CH$_2$), 1.56-1.44 (m, 4H, CH$_2$×2), 1.34-1.20 (m, 4H, CH$_2$×2); $^{13}$C NMR (DMSO-d$_6$) δ: 167.12 (C), 167.08 (C), 165.83 (C), 157.92 (C), 156.30 (C), 149.58 (CH, Py), 145.23 (C), 136.12 (CH, Py), 136.03 (C), 135.16 (CH), 135.00 (C), 132.13 (C), 129.54 (CH), 127.74 (CH), 127.62 (CH), 126.51 (CH), 123.89 (CH, Py), 123.31 (CH), 122.93 (CH), 113.08 (CH), 85.11 (C), 63.56 (CH$_2$), 62.65 (CH$_2$), 54.97 (CH$_3$), 37.96 (CH$_2$), 35.65 (CH$_2$), 29.37 (CH$_2$), 28.60 (CH$_2$), 28.27 (CH$_2$), 25.48 (CH$_2$), 25.19 (CH$_2$).

1-[(4-Pentafluorophenoxycarbonylphthalimidylpropyl)aminocarbonyl]oxy-O-(dimethoxytrityl)-6-hexanol (compound 5b)

404 mg (yield: 94%) of the title compound (compound 5b) was obtained as a yellow foam by the same treatment as in the synthesis of compound 5a using 387 mg (0.50 mmol) of 1-[(4-carboxyphthalimidylpropyl)aminocarbonyl]oxy-O-(dimethoxytrityl)-6-hexanol (compound 4b, pyridine salt) as a starting material.

ESI-MS Calculated: 883.2624 (C$_{46}$H$_{41}$F$_5$N$_2$O$_9$Na [M+Na]$^+$). Found: 883.2625. $^1$H NMR (DMSO-d$_6$) δ: 8.59 (m, 1H, Phth), 8.45 (m 1H, Phth), 8.11 (d, 1H, Phth, J=7.9 Hz), 7.41-7.18 (m, 9H, DMT), 7.10 (br t, 1H, NH, J=6.3 Hz), 6.87 (d, 4H, DMT, J=8.3 Hz), 3.87 (t, 2H, CH$_2$, J=6.4 Hz), 3.72 (s, 6H, OCH$_3$×2), 3.63 (t, 2H, CH$_2$, J=7.1 Hz), 3.03 (q, 2H, CH$_2$, J=6.3 Hz), 2.94 (t, 2H, CH$_2$, J=6.3 Hz), 1.77 (m, 2H, CH$_2$), 1.57-1.45 (m, 4H, CH$_2$×2), 1.28 (m, 4H, CH$_2$×2).

revPro Linker-CPG Solid-Phase Carrier (Compound 6b)

The title compound (compound 6b) (31.7 μmol/g) was obtained by the same treatment as in the synthesis of compound 6a using 86.1 mg (0.10 mmol) of 1-[(4-pentafluorophenoxycarbonylphthalimidylpropyl)aminocarbonyl]oxy-O-(dimethoxytrityl)-6-hexanol (compound 5b) as a starting material.

Example 3

Synthesis of revH Linker-Polystyrene Solid-Phase Carrier (Compound 6c)

revH Linker-Polystyrene Solid-Phase Carrier (Compound 6c)

In a glass vial, 84.7 mg (0.10 mmol) of 1-[(4-pentafluorophenoxycarbonylphthalimidylethyl)aminocarbonyl]oxy-O-(dimethoxytrityl)-6-hexanol (compound 5a) was dissolved in 3 ml of a mixed solution of dimethylformamide and pyridine (9:1). To the solution, 400 mg of an aminated polystyrene carrier material was added, and the mixture was vigorously shaken at room temperature for 24 hours. The polystyrene solid-phase carrier was washed with dimethylformamide (5 ml×4), methanol (10 ml×2), and methylene chloride (10 ml×2) and then dried under reduced pressure at room temperature for 2 hours. Subsequently, 5 ml of a capping solution (mixed solution of pyridine and acetic anhydride (9:1) containing 0.1 M dimethylaminopyridine) was added to the polystyrene solid-phase carrier, and the mixture was vigorously shaken at room temperature for 2 hours. The polystyrene solid-phase carrier was washed with pyridine (5 ml×4), methanol (10 ml×2), and methylene chloride (10 ml×2) and then dried under reduced pressure at room temperature to obtain the title compound (compound 8c) (120.5 mmol/g).

Comparative Example 1

C6 Linker-CPG Solid-Phase Carrier

A commercially available resin for amination modification (3'-PT-Amino-modifier C6 CPG, Glen Research Corp.) was used.

Comparative Example 2

Synthesis of ssH Linker-CPG Solid-Phase Carrier

A solid-phase carrier for 3' amination modification of an oligonucleotide probe described in Patent Literature 1 was synthesized according to the following scheme 2:

Scheme 2

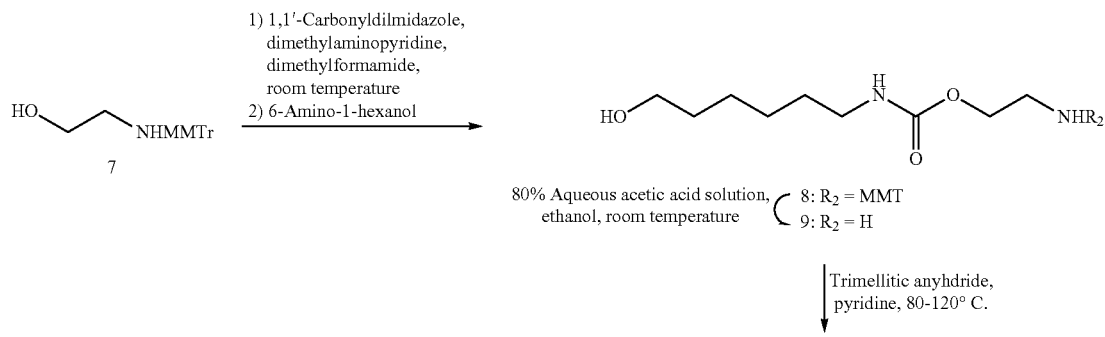

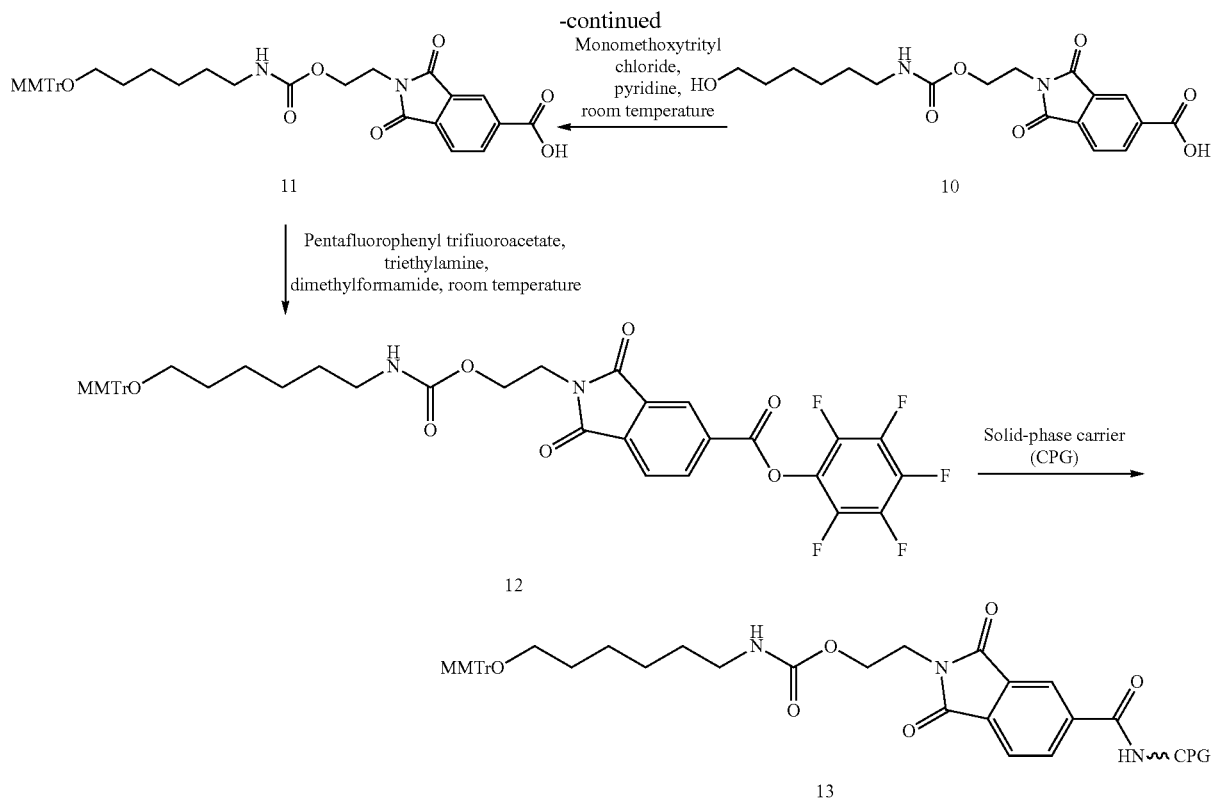

N-[2-(Monomethoxytrityl)aminoethoxycarbonyl]-6-amino-1-hexanol (compound 8)

In an argon atmosphere, 6.67 g (20.0 mmol) of 2-(monomethoxytrityl)aminoethanol (compound 7) and 490 mg (4.00 mmol) of dimethylaminopyridine were dissolved in 120 ml of dimethylformamide. To the solution, 1.95 g (12.0 mmol) of 1,1'-carbonyldiimidazole was added, and the mixture was stirred at room temperature. After 2 hours, 1.95 g (12.0 mmol) of 1,1'-carbonyldiimidazole was further added, and the mixture was stirred at room temperature for additional 4 hours. Subsequently, 7.03 g (60.0 mmol) of 6-amino-1-hexanol was added to the reaction solution, and the mixture was stirred at room temperature for 20 hours. 350 ml of ethyl acetate was added to the reaction solution, and the mixture was washed with 100 ml of water four times and 100 ml of saturated saline once and dried over sodium sulfate. The solution was concentrated under reduced pressure. Then, the residue was purified by silica gel column chromatography (elution solvent: ethyl acetate-hexane) to obtain 8.35 g (yield: 88%) of the title compound (compound 8) as a colorless goo.

FAB-LRMS m/z 477.3 [M+H]$^+$; FAB-HRMS Calculated: 477.2753 ($C_{29}H_{37}N_2O_4$ [M+H]$^+$). Found: 477.2760. $^1$H NMR (270 MHz, DMSO-$d_6$) δ: 7.40-7.38 (m, 4H, MMT), 7.30-7.25 (m, 6H, MMT), 7.19-7.14 (m, 2H, MMT), 7.11 (t, 1H, NH, J=5.6 Hz), 6.87-6.83 (m, 2H, MMT), 4.33 (t, 1H, OH, J=5.3 Hz), 4.02 (t, 2H, $CH_2$, J=5.7 Hz), 3.72 (s, 3H, $OCH_3$), 3.36 (dt, 2H, $CH_2$, J=5.3, 6.5 Hz), 2.94 (dt, 2H, $CH_2$, J=5.6, 6.9 Hz), 2.69 (t, 1H, NH, J=7.9 Hz), 2.14 (dt, 2H, $CH_2$, J=7.9, 5.7 Hz), 1.43-1.33 (m, 4H, $CH_2×2$), 1.28-1.21 (m, 4H, $CH_2×2$); $^{13}$C NMR (67.8 MHz, DMSO-$d_6$) δ: 156.99 (C), 155.87 (C), 145.92 (C), 137.49 (C), 129.19 (CH), 127.91 (CH), 127.39 (CH), 125.68 (CH), 112.75 (CH), 69.37 (C), 63.32 ($CH_2$), 60.45 ($CH_2$), 54.75 ($CH_3$), 42.98 ($CH_2$), 40.02 ($CH_2$), 32.33 ($CH_2$), 29.39 ($CH_2$), 26.04 ($CH_2$), 25.10 ($CH_2$).

N-(2-Aminoethoxycarbonyl)-6-amino-1-hexanol (compound 9)

In an argon atmosphere, 5.87 g (12.32 mmol) of N-[2-(monomethoxytrityl)aminoethoxycarbonyl]-6-amino-1-hexanol (compound 8) was dissolved in 70 ml of ethanol. To the solution, 50 ml of an 80% aqueous acetic acid solution was added, and the mixture was stirred at room temperature for 1.5 hours. The reaction solution was concentrated under reduced pressure, followed by azeotropy with ethanol (20 ml×3). The residue was dissolved in 150 ml of water. The solution was washed with 70 ml of diethyl ether twice. The solution was concentrated into approximately 70 ml under reduced pressure. Then, the pH of the solution was adjusted to 12 by the addition of a 1 N aqueous sodium hydroxide solution. The residue was purified by reverse-phase silica gel column chromatography (elution solvent: acetonitrile-water) to obtain 2.11 g (yield: 84%) of the title compound (compound 9) as a white solid.

EI-LRMS m/z 205 [M+H]$^+$; EI-HRMS Calculated: 205.1552 ($C_9H_{21}N_2O_3$ [M+H]$^+$). Found: 205.1546. $^1$H NMR (270 MHz, DMSO-$d_6$) δ: 7.03 (br t, 1H, NH, J=5.6 Hz), 3.85 (t, 2H, $CH_2$, J=6.1 Hz), 3.37 (t, 2H, $CH_2$, J=6.5 Hz), 2.94 (dt, 2H, $CH_2$, J=5.6, 6.9 Hz), 2.67 (t, 2H, $CH_2$, J=6.1 Hz), 1.41-1.35 (m, 4H, $CH_2×2$), 1.27-1.23 (m, 4H, $CH_2×2$); $^{13}$C NMR (67.8 MHz, DMSO-$d_6$) δ: 156.22 (C), 66.10 ($CH_2$), 60.54 ($CH_2$), 40.84 ($CH_2$), 40.06 ($CH_2$), 32.38 ($CH_2$), 29.38 ($CH_2$), 26.06 ($CH_2$), 25.12 ($CH_2$).

N-[(4-Carboxyphthalimidyl)ethoxycarbonyl]-6-amino-1-hexanol (10)

295 mg (yield: 78%) of the title compound (compound 10) was obtained as a white foam by the same treatment as in the synthesis of compound 3a using 204 mg (1.00 mmol) of N-(2-aminoethoxycarbonyl)-6-amino-1-hexanol (compound 9) as a starting material.

ESI-MS Calculated: 377.1354 ($C_{18}H_{21}N_2O_7$ [M–H]$^-$). Found: 377.1353. $^1$H NMR (DMSO-$d_6$) δ: 13.68 (br s, 1H, COOH), 8.36 (dd, 1H, Phth, J=1.3, 7.7 Hz), 8.23 (s, 1H, Phth), 7.99 (d, 1H, Phth, J=7.7 Hz), 7.06 (t, 1H, NH, J=5.6 Hz), 4.30 (br s, 1H, OH), 4.19 (t, 2H, CH$_2$, J=5.3 Hz), 3.81 (t, 2H, CH$_2$, J=5.3 Hz), 3.35 (t, 2H, CH$_2$, J=6.3 Hz), 2.83 (dt, 2H, CH$_2$, J=5.6, 6.3 Hz), 1.35 (m, 2H, CH$_2$), 1.27-1.12 (m, 6H, CH$_2$×3); $^{13}$C NMR (DMSO-$d_6$) δ: 166.83 (C), 166.80 (C), 165.69 (C), 155.73 (C), 136.24 (C), 135.20 (CH), 134.76 (C), 131.93 (C), 123.35 (CH), 122.93 (CH), 60.54 (CH$_2$), 60.17 (CH$_2$), 40.02 (CH$_2$), 37.64 (CH$_2$), 32.35 (CH$_2$), 29.19 (CH$_2$), 25.90 (CH$_2$), 25.07 (CH$_2$).

N-[(4-Carboxyphthalimidyl)ethoxycarbonyl]-6-amino-O-(monomethoxytrityl)-1-hexanol (compound 11)

757 mg (2.00 mmol) of N-[(4-carboxyphthalimidyl)ethoxycarbonyl]-6-amino-1-hexanol (compound 10) was dissolved in 20 ml of pyridine. To the solution, 1.24 g (4.00 mmol) of monomethoxytrityl chloride was added, and the mixture was stirred at room temperature for 18 hours. 5 ml of ethanol was added to the reaction solution, and the mixture was then concentrated under reduced pressure. The residue was dissolved in 200 ml of ethyl acetate. The solution was washed with 70 ml of water twice and 70 ml of saturated saline once and dried over sodium sulfate. The solution was concentrated under reduced pressure, followed by azeotropy with toluene (10 ml×2). The residue was purified by silica gel column chromatography (elution solvent: ethanol-chloroform) to obtain 918 mg (yield: 71%) of the title compound (compound 11) as a white foam.

ESI-MS Calculated: 673.2526 ($C_{38}H_{38}N_2O_8Na$ [M+Na]$^+$). Found: 673.2518. $^1$H NMR (DMSO-$d_6$) δ: 8.34 (d, 1H, Phth, J=7.7 Hz), 8.23 (s, 1H, Phth), 7.97 (d, 1H, Phth, J=7.7 Hz), 7.41-7.29 (m, 8H, MMT), 7.25-7.21 (m, 4H, MMT), 7.09 (br t, 1H, NH, J=5.3 Hz), 6.89 (m, 2H, MMT), 4.18 (t, 2H, CH$_2$, J=5.3 Hz), 3.81 (t, 2H, CH$_2$, J=5.3 Hz), 3.73 (s, 3H, OCH$_3$), 2.93 (t, 2H, CH$_2$, J=6.3 Hz), 2.83 (dt, 2H, CH$_2$, J=5.3, 6.7 Hz), 1.50 (m, 2H, CH$_2$), 1.30-1.18 (m, 4H, CH$_2$×2), 1.13 (m, 2H, CH$_2$); $^{13}$C NMR (DMSO-$d_6$) δ: 166.98 (C), 165.92 (C), 158.05 (C), 155.82 (C), 144.68 (C), 136.95 (C), 135.47 (C), 135.23 (CH), 134.67 (C), 131.98 (C), 129.86 (CH), 127.90 (CH), 127.82 (CH), 126.72 (CH), 123.35 (CH), 123.05 (CH), 113.14 (CH), 85.41 (C), 62.76 (CH$_2$), 60.34 (CH$_2$), 55.00 (CH$_3$), 40.06 (CH$_2$), 37.71 (CH$_2$), 29.34 (CH$_2$), 29.18 (CH$_2$), 25.88 (CH$_2$), 25.42 (CH$_2$).

N-[(4-Pentafluorophenoxycarbonylphthalimidyl)ethoxycarbonyl]-6-amino-O-(monomethoxytrityl)-1-hexanol (12)

300 mg (yield: 89%) of the title compound (compound 12) was obtained as a white foam by the same treatment as in the synthesis of compound 5a using 260 mg (0.40 mmol) of N-[(4-carboxyphthalimidyl)ethoxycarbonyl]-6-amino-O-(monomethoxytrityl)-1-hexanol (compound 11) as a starting material.

ESI-MS Calculated: 839.2368 ($C_{44}H_{37}F_5N_2O_8Na$ [M+Na]$^+$). Found: 839.2353. $^1$H NMR (DMSO-$d_6$) δ: 8.55 (dd, 1H, Phth, J=1.3, 7.7 Hz), 8.45 (s, 1H, Phth), 8.11 (d, 1H, Phth, J=7.7 Hz), 7.36-7.26 (m, 8H, MMT), 7.22-7.18 (m, 4H, MMT), 7.07 (br t, 1H, NH, J=5.5 Hz), 6.88-6.84 (m, 2H, MMT), 4.19 (t, 2H, CH$_2$, J=5.3 Hz), 3.83 (t, 2H, CH$_2$, J=5.3 Hz), 3.71 (s, 3H, OCH$_3$), 2.91 (t, 2H, CH$_2$, J=6.5 Hz), 2.79 (dt, 2H, CH$_2$, J=5.5, 6.5 Hz), 1.48 (m, 2H, CH$_2$), 1.26-1.05 (m, 6H, CH$_2$×3).

ssH Linker-CPG Solid-Phase Carrier (Compound 13)

The title compound (compound 13) (28.5 μmol/g) was obtained by the same treatment as in the synthesis of compound 8a using 85.0 mg (0.10 mmol) of N-[(4-pentafluorophenoxycarbonylphthalimidyl)ethoxycarbonyl]-6-amino-O-(monomethoxytrityl)-1-hexanol (compound 12) as a starting material.

Synthesis Example 2

Synthesis of Deoxyoligonucleotide Probe 0.2 μmol equivalents of the solid-phase carriers for 3' amination modification of Example 1 (revH linker-CPG), Example 2 (revPro linker-CPG), Comparative Example 1 (C6 linker-CPG), and Comparative Example 2 (ssH linker-CPG) were each weighed. On each solid-phase carrier, deoxynucleoside 3'-phosphoramidites (Glen Research Corp.) were sequentially condensed according to the sequence to synthesize 3'-aminated oligonucleotides with a 5-base or 25-base strand length containing the amino linker of Example 1 or 2 or Comparative Example 1 or 2.

The synthesis of the 3'-aminated oligonucleotides was performed using an automatic DNA synthesizer (model 3900; manufactured by Applied Biosystems division, PerkinElmer Co., Ltd). The synthesized 3'-aminated oligonucleotides were deprotected and then purified by preparative HPLC.

The HPLC analysis was conducted using an apparatus (Gilson, Inc.) connected with Waters 996 photodiode array detector (Waters Corp.). Waters μ-Bondasphere C18, 300 Å (inner diameter 3.9 mm×length 150 mm, Waters Corp.) was used as a column for reverse-phase analysis, and GL Science Inertsil ODS-3 C18 (inner diameter 8.0 mm×length 300 mm, GL Science Inc.) was used as a column for reverse-phase fractionation. A concentration gradient of acetonitrile in a 0.1 M triethylammonium acetate buffer solution (TEAA, pH 7.0) was used as a mobile phase for reverse phase. The molecular weight of each purified aminated oligonucleotide was measured by MALDI-TOFMS to confirm that the molecule of interest was obtained.

Results of Molecular Weight Measurement

T5-revH ($C_{59}H_{84}N_{12}O_{38}P_5$)$^-$, Calculated: m/e 1723.370. Found: 1723.750.

T5-revPro ($C_{60}H_{86}N_{12}O_{38}P_5$)$^-$, Calculated: m/e 1737.385. Found: 1737.797.

T5-C6 ($C_{56}H_{79}N_{11}O_{36}P_5$)$^-$, Calculated: m/e 1636.338. Found: 1636.819.

Sp25-revH ($C_{252}H_{325}N_{95}O_{150}P_{25}$)$^-$, Calculated: m/e 7857.423. Found: 7857.657.

Sp25-revPro ($C_{253}H_{327}N_{95}O_{150}P_{25}$)$^-$, Calculated: m/e 7871.439. Found: 7872.029.

Sp25-C6 ($C_{249}H_{320}N_{94}O_{148}P_{25}$)$^-$, Calculated: m/e 7770.391. Found: 7770.082.

Sequence of 5-base 3'-aminated oligonucleotide (T5-X; X=C6, ssH, revH, or revPro):

5' TTTTT-X 3'

(X=C6, ssH, revH, or revPro)

Sequence of 25-base 3'-aminated oligonucleotide (Sp25-X; X=C6, ssH, revH, or revPro):

5' TCTTCCAAGCAATTCCAATGAAAGC-X 3'   (SEQ ID NO: 1)

In the formula, X is C6 linker-CPG, ssH linker-CPG, revH linker-CPG, or revPro linker-CPG.

Synthesis Example 3

Synthesis of Oligoribonucleotide Probe 0.2 mmol equivalents of the solid-phase carrier for 3' amination modification of Example 1 (revH linker-CPG) were weighed. On the solid-phase carrier, 2'-O-TBDMS-3'-phosphoramidites (Glen Research Corp.) were sequentially condensed according to the sequence to synthesize a 3'-revH-bound oligoribonucleotide (r20-revH) with a 20-base strand length.

The synthesis of the 3'-aminated oligoribonucleotide was performed using an automatic DNA synthesizer (model 3900; manufactured by Applied Biosystems division, PerkinElmer Co., Ltd).

The synthesized oligonucleotide-bound CPG was treated at 65° C. for 10 minutes in an AMA solution [40% methylamine:concentrated ammonia water (1:1)] (1.5 ml), and the solvent was evaporated off. Subsequently, dimethyl sulfoxide (115 µl), triethylamine (60 µl), and triethylamine-hydrogen trifluoride (75 µl) were added to the residue. The vessel was hermetically sealed and heated at 65° C. for 2.5 hours. 250 µl of 0.2 M triethylammonium acetate (pH 7.0) was added thereto, and the mixture was desalted with NAP10 (GE Healthcare Japan Corp.). The obtained oligonucleotide-containing solution was purified by reverse-phase HPLC.

The HPLC analysis was conducted using an apparatus (Gilson, Inc.) connected with Waters µ-Bondasphere C18, 300 Å (inner diameter 3.9 mm×length 150 mm, Waters Corp.). A concentration gradient of acetonitrile in a 0.1 M triethylammonium acetate buffer solution (TEAA, pH 7.0) was used as a mobile phase for reverse phase.

The molecular weight of the purified 3'-revH-bound oligoribonucleotide was measured by MALDI-TOFMS to confirm that the molecule of interest was obtained.

Results of molecular weight measurement r20-revH $(C_{197}H_{254}N_{73}O_{141}P_{20})^-$, Calculated: m/e 6518.977. Found: 6518.982.

Sequence of 20-base 3'-revH-bound oligoribonucleotide (r20-revH):

5' AAACCUCUUCCAAGCAAUUC-X 3'   (SEQ ID NO: 2)

In the formula, X is revH linker-CPG.
Reverse-phase HPLC analysis conditions:
Mobile Phase
Solution A: 5% acetonitrile/0.1 M TEAA (pH 7.0)
Solution B: 25% acetonitrile/0.1 M TEAA (pH 7.0)
Elution Conditions
Percentage of solution B: 15-35%120 min
Column
Waters µ-Bondasphere C18, 300 Å (inner diameter 3.9 mm×length 150 mm, Waters Corp.)

Use Example 1

Confirmation of Excision Treatment from Solid-Phase Carrier

Figure 2:
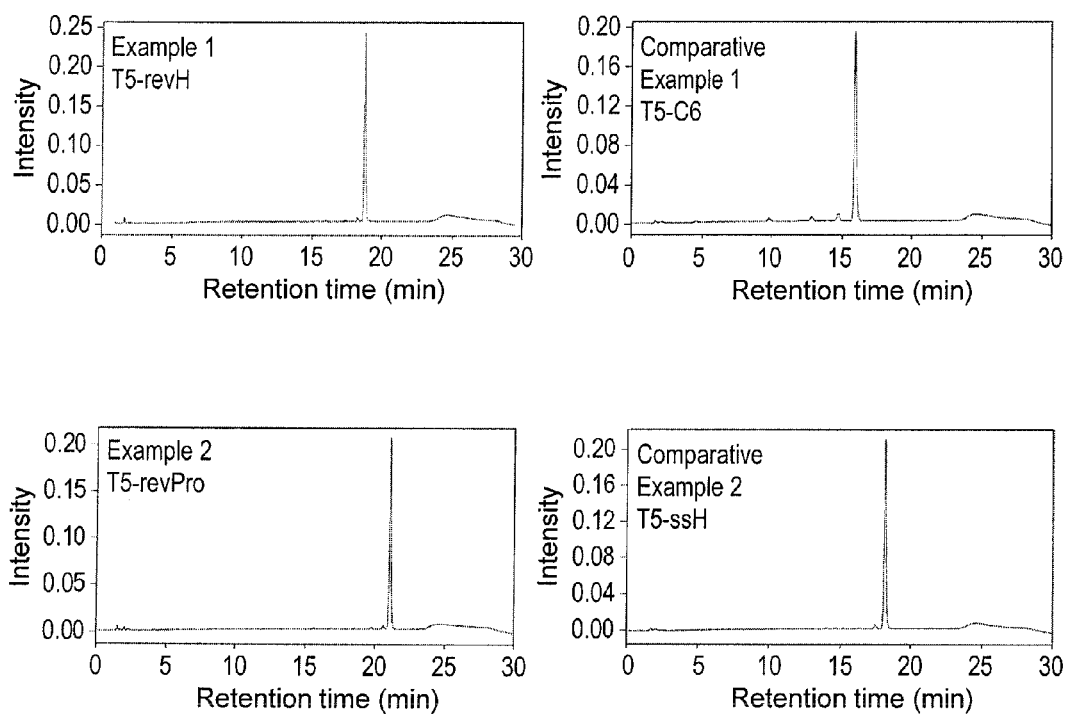
FIG. 2 is a diagram showing results of reverse-phase HPLC analysis of a reaction solution after AMA treatment of a 5-base oligonucleotide (T5-X) synthesized using a solid-phase carrier for 3' amination modification of Example 1 or 2 or Comparative Example 1 or 2.

After the synthesis of the 5-base oligonucleotide bound with the solid-phase carrier for 3' amination modification of Example 1 or 2 or Comparative Example 1 or 2 (T5-revH-CPG, T5-revPro-CPG, T5-C6-CPG, or T5-ssH-CPG), 0.1 µmol equivalents (based on each solid-phase carrier) of the oligonucleotide bound with the solid-phase carrier for 3' amination modification was weighed into a sealed vial and treated under deprotection conditions described below. Then, a 20 µl aliquot was sampled from each reaction solution, and the solvent was evaporated off under reduced pressure. Then, the residue was dissolved in 25 µl of sterilized water and analyzed by reverse-phase HPLC. The analysis results of each sample are shown in FIG. 2.

3'-Aminated Oligonucleotide Excision Conditions from Solid-Phase Carrier:

AMA solution [40% methylamine:concentrated ammonia water (1:1)] (2 ml, 65° C., 10 min)

From the results, the 3'-aminated oligonucleotide comprising the amino linker of the present invention was confirmed to be recovered from the solid-phase carrier without being decomposed in the AMA solution.

Use Example 2

Confirmation of Stability Under Alkaline Conditions

The excision of the oligonucleotide moiety from the carrier in the solid-phase carrier-bound oligonucleotide synthesized in the solid phase and the deprotection of the protective group in the oligonucleotide moiety are typically performed under alkaline conditions. Thus, the following experiment was conducted in order to clearly evaluate the stability of the amino linker under alkaline conditions.

Figure 3:
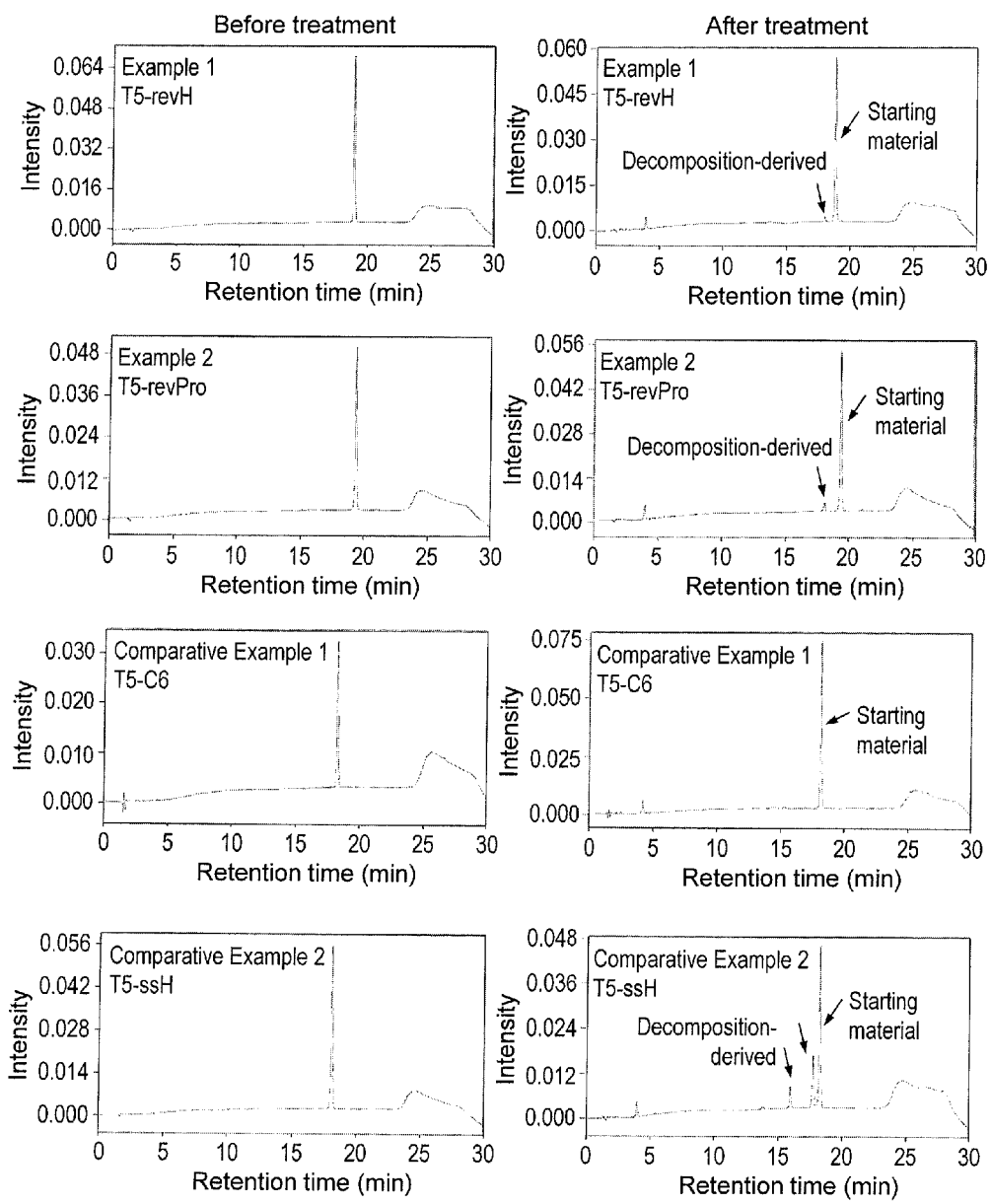
FIG. 3 is a diagram showing analysis results of reverse-phase HPLC performed before and after concentrated ammonia water treatment (heating at 65° C. for 16 hours) of a 3'-aminated oligonucleotide of Example 1 or 2 or Comparative Example 1 or 2.
Figure 4:
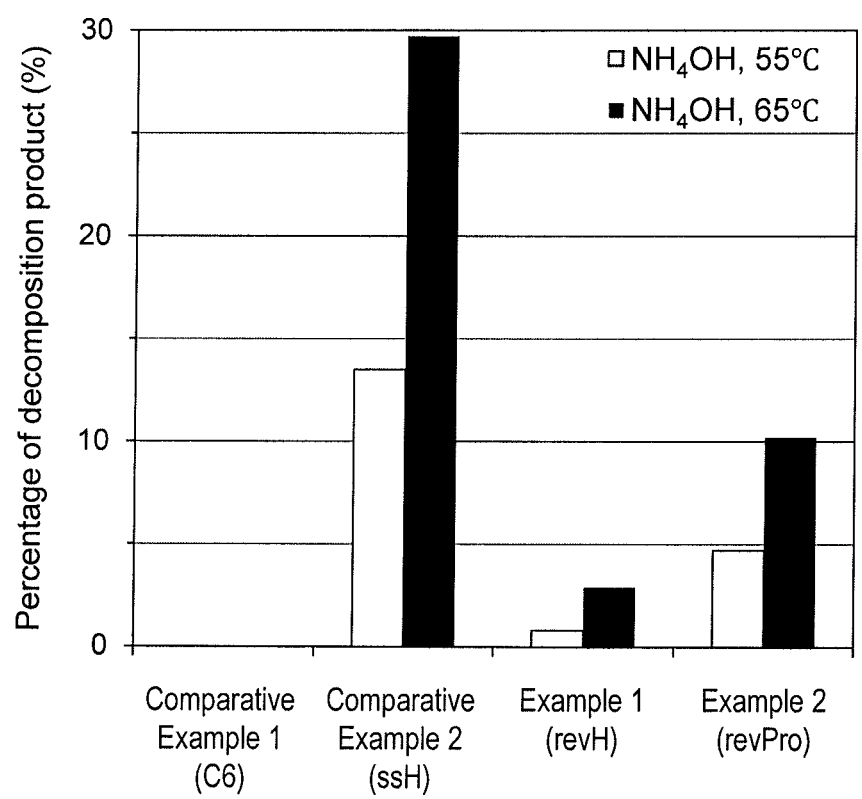
FIG. 4 is a diagram showing the ratio (%) of the amount of T5-X decomposed by concentrated ammonia water treatment to the total amount of the 3'-aminated oligonucleotide (T5-X) after the concentrated ammonia water treatment, wherein the treatment was performed for 16 hour hours with concentrated ammonia water of 55° C. or 65° C.

First, the 5-base oligonucleotide bound with the solid-phase carrier for 3' amination modification of Example 1 or 2 or Comparative Example 1 or 2 (T5-revH-CPG, T5-revPro-CPG, T5-C6-CPG, or T5-ssH-CPG; synthesized in Synthesis Example 2) was treated under condition 2 (AMA solution) of Use Example 1. Subsequently, the oligonucleotide was purified using reverse-phase HPLC and then quantified by the measurement of absorbance at 260 nm. Next, each purified 5-base 3'-aminated oligonucleotide (T5-X, 1.5 nmol) was collected into a tube, and the solvent was evaporated off under reduced pressure. Concentrated ammonia water (100 µl) was added to the residue, and the mixture was heated at 55° C. or 65° C. for 16 hours. The solvent was evaporated off under reduced pressure. Then, the residue was dissolved in 60 µl of sterilized water. The reaction solution was analyzed by reverse-phase HPLC. FIG. 3 shows HPLC analysis results of the reaction solution heat-treated at 65° C. for 16 hours. FIG. 4 shows the ratio (%) of the amount of T5-X decomposed by concentrated ammonia water treatment (55° C. or 65° C.) to the total amount of the 3'-aminated oligonucleotide (T5-X).

As shown in FIGS. 3 and 4, the 5-base 3'-aminated oligonucleotide (T5-ssH) comprising the amino linker of Comparative Example 2 was decomposed approximately 13% under the condition of 55° C. and approximately 30% under the condition of 65° C. By contrast, the ratio of the decomposition product of the 5-base 3'-aminated oligonucleotide (T5-revH) comprising the amino linker of Example 1 was less than approximately 3% under the condition of 65° C. The ratio of the decomposition product of the 5-base 3'-aminated oligonucleotide (T5-revPro) comprising the amino linker of Example 2 was approximately 10% under the condition of 65° C.

These results demonstrated that the 3'-aminated oligonucleotide comprising the amino linker of the present invention can be stably present even when heated under alkaline conditions.

Reverse-phase HPLC analysis conditions:
Mobile Phase
Solution A: 5% acetonitrile/0.1 M TEAA (pH 7.0)
Solution B: 25% acetonitrile/0.1 M TEAA (pH 7.0)
Elution Conditions
Percentage of solution B: 0-50%/20 min Use Example 3

Excision and Purification of Sp25-X from Solid-Phase Carrier 2 ml of an AMA solution was added to the 25-base oligonucleotide bound with the solid-phase carrier for 3' amination modification of Example 1 or 2 or Comparative Example 1 or 2 (Sp25-revH-CPG, Sp25-revPro-CPG, Sp25-C6-CPG, or Sp25-ssH-CPG) and reacted at 65° C. for 10 minutes to perform the excision of the 3'-aminated oligonucleotide from the solid-phase carrier and the deprotection treatment thereof. The solvent was evaporated off under reduced pressure. Then, the residue was dissolved in sterilized water. The oligonucleotide of interest was purified by reverse-phase HPLC.

Reverse-Phase HPLC Fractionation Conditions:
Mobile Phase
Solution A: 5% acetonitrile/0.1 M TEAA (pH 7.0)
Solution B: 25% acetonitrile/0.1 M TEAA (pH 7.0)
Elution Conditions
Percentage of solution B: 20-40%/20 min (used in the purification of Sp25-revPro, Sp25-C6, and Sp25-ssH)
Percentage of solution B: 25-45%/20 min (used in the purification of Sp25-revH)

Use Example 4

Reaction with Fluorescein Isothiocyanate (FITC)

Figure 5:
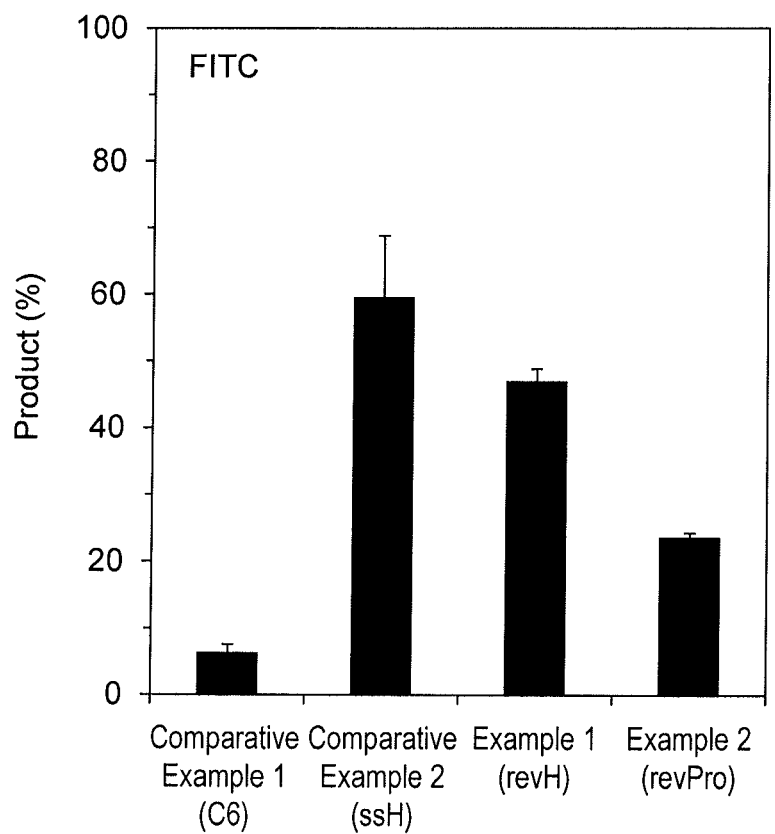
FIG. 5 is a diagram showing the ratio (%) of the amount (mol) of a FITCylation reaction product to the total amount (mol) of the starting material Sp25-X.

The 3'-aminated oligonucleotide (Sp25-revH, Sp25-C6, or Sp25-ssH) (150 pmol) comprising the amino linker of Example 1 or Comparative Example 1 or 2 and FITC (Dojindo Laboratories) (150 nmol) were dissolved in 10% (v/v) dimethylformamide and a 0.25 M phosphate buffer solution (pH 8.0) (total amount: 100 μl). The reaction was started at 40° C. with light shielded. 60 minutes after the start of the reaction, the reaction solution was desalted with NAP5 (GE Healthcare Japan Corp.). The eluate was analyzed by reverse-phase HPLC. FIG. 5 shows the ratio (%) of the amount (mol) of the reaction product to the total amount (mol) of the starting material Sp25-X.

Reverse-Phase HPLC Analysis Conditions:
Mobile Phase
Solution A: 5% acetonitrile/0.1 M TEAA (pH 7.0)
Solution B: 50% acetonitrile/0.1 M TEAA (pH 7.0)
Elution Conditions
Percentage of solution B: 0-100%/20 min
Column
Waters μ-Bondasphere C18, 300 Å (inner diameter 3.9 mm×length 150 mm, Waters Corp.)

Use Example 5

Reaction with Biotin Succinimidyl Ester

Figure 6:
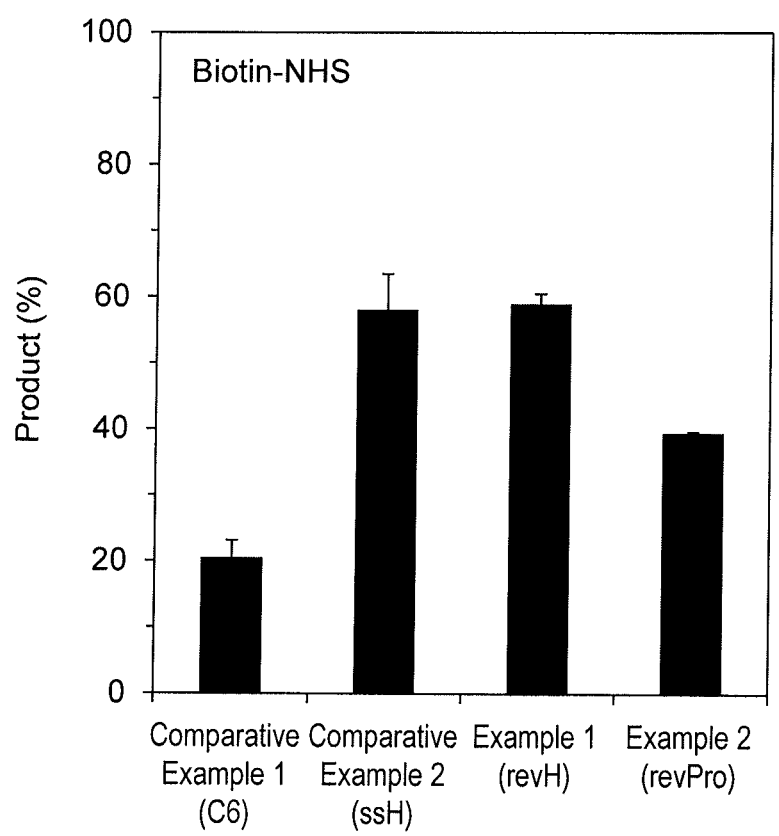
FIG. 6 is a diagram showing the ratio (%) of the amount (mol) of a biotinylation reaction product to the total amount (mol) of the starting material Sp25-X.

The 3'-aminated oligonucleotide (Sp25-revH, Sp25-C6, or Sp25-ssH) (150 pmol) comprising the amino linker of Example 1 or Comparative Example 1 or 2 and biotin succinimidyl ester (Dojindo Laboratories) (15 nmol) were dissolved in a 0.25 M phosphate buffer solution (pH 8.0) (total amount: 100 μl). The reaction was started at 40° C. 30 minutes after the start of the reaction, the reaction solution was desalted with NAP5 (GE Healthcare Japan Corp.). The eluate was analyzed by reverse-phase HPLC. FIG. 6 shows the ratio (%) of the amount (mol) of the reaction product to the total amount (mol) of the starting material Sp25-X.

Reverse-Phase HPLC Analysis Conditions:
Mobile Phase
Solution A: 5% acetonitrile/0.1 M TEAA (pH 7.0)
Solution B: 25% acetonitrile/0.1 M TEAA (pH 7.0)
Elution Conditions
Percentage of solution B: 0-80%/20 min
Column
Waters μ-Bondasphere C18, 300 Å (inner diameter 3.9 mm×length 150 mm, Waters Corp.)

Use Example 6

Reaction with Polyethylene Glycol Succinimidyl Ester

Figure 7:
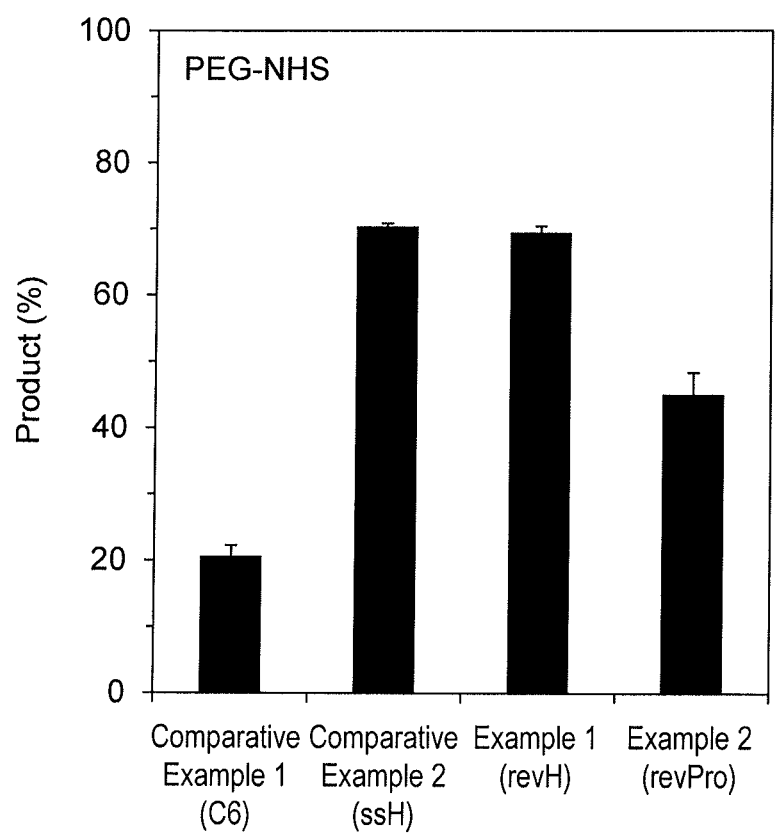
FIG. 7 is a diagram showing the ratio (%) of the amount (mol) of a PEGylation reaction product to the total amount (mol) of the starting material Sp25-X.
Figure 8:
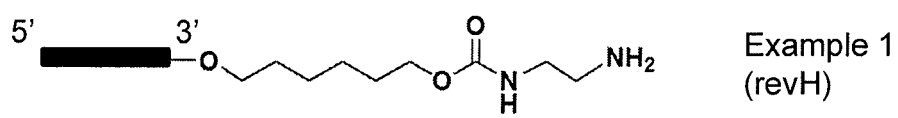
FIG. 8 is a diagram showing another embodiment of the aminated oligonucleotide of the present invention.
Figure 8:
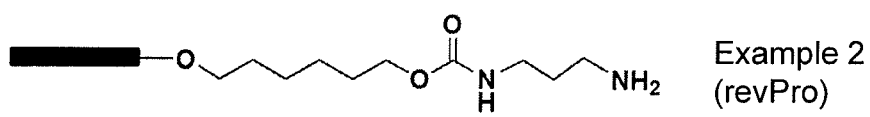
Figure 8:
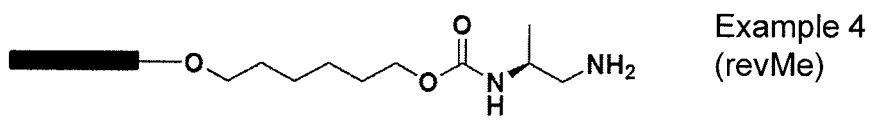
Figure 8:
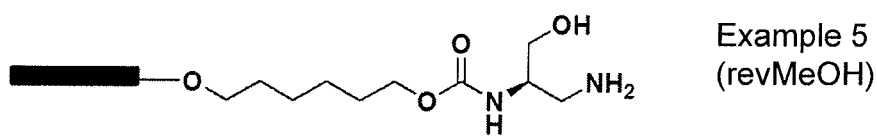

The 3'-aminated oligonucleotide (Sp25-revH, Sp25-C6, or Sp25-ssH) (150 pmol) comprising the amino linker of Example 1 or Comparative Example 1 or 2 and polyethylene glycol succinimidyl ester (40K; NOF Corp.) (75 nmol) were dissolved in a 0.25 M phosphate buffer solution (pH 8.0) (total amount: 100 μl). The reaction was started at 40° C. 60 minutes after the start of the reaction, the reaction solution was desalted with NAP5 (GE Healthcare Japan Corp.). The eluate was analyzed by reverse-phase HPLC. FIG. 7 shows the ratio (%) of the amount (mol) of the reaction product to the total amount (mol) of the starting material Sp25-X.

Reverse-Phase HPLC Analysis Conditions:
Mobile Phase
Solution A: 20% acetonitrile
Solution B: 2 M ammonium formate/20% acetonitrile
Elution Conditions
Percentage of solution B: 5-70%/20 min
Column
Waters μ-Bondasphere C18, 300 Å (inner diameter 3.9 mm×length 150 mm, Waters Corp.)

As shown in FIGS. 5 to 7, the 3'-aminated oligonucleotide comprising the amino linker of the present invention was reacted with FITC and active ester with significantly higher reaction efficiency than that of the 3'-aminated oligonucleotide comprising the C6 linker of the conventional technique (Comparative Example 1). Also, the 3'-aminated oligonucleotide comprising the amino linker of the present invention was reacted with FITC and active ester with reaction efficiency substantially equivalent to that of the 3'-aminated oligonucleotide comprising the ssH linker described in Patent Literature 1 (Comparative Example 2).

Synthesis Example 4

Synthesis of Solid-Phase Carrier for 3' Amination Modification

Example 4

Synthesis of revMe Linker-CPG Solid-Phase Carrier (Compound 19)

A solid-phase carrier for 3' amination modification was synthesized according to the following scheme 3:

mmol) of triethylamine and 490 mg (3.00 mmol) of 1,1'-carbonyldiimidazole were added, and the mixture was stirred at room temperature for 5 hours. Subsequently, 623 mg (5.00 mmol) of L-alaninamide hydrochloride and 31 mg (0.25 mmol) of dimethylaminopyridine were added to the reaction solution, and the mixture was stirred at 80° C. for 24 hours. 150 ml of ethyl acetate was added to the reaction solution, and the mixture was washed with 50 ml of water four times and 50 ml of saturated saline once and dried over sodium sulfate. The solution was concentrated under reduced pressure. Then, the residue was purified by silica gel column chromatography (elution solvent: ethanol-chloro-

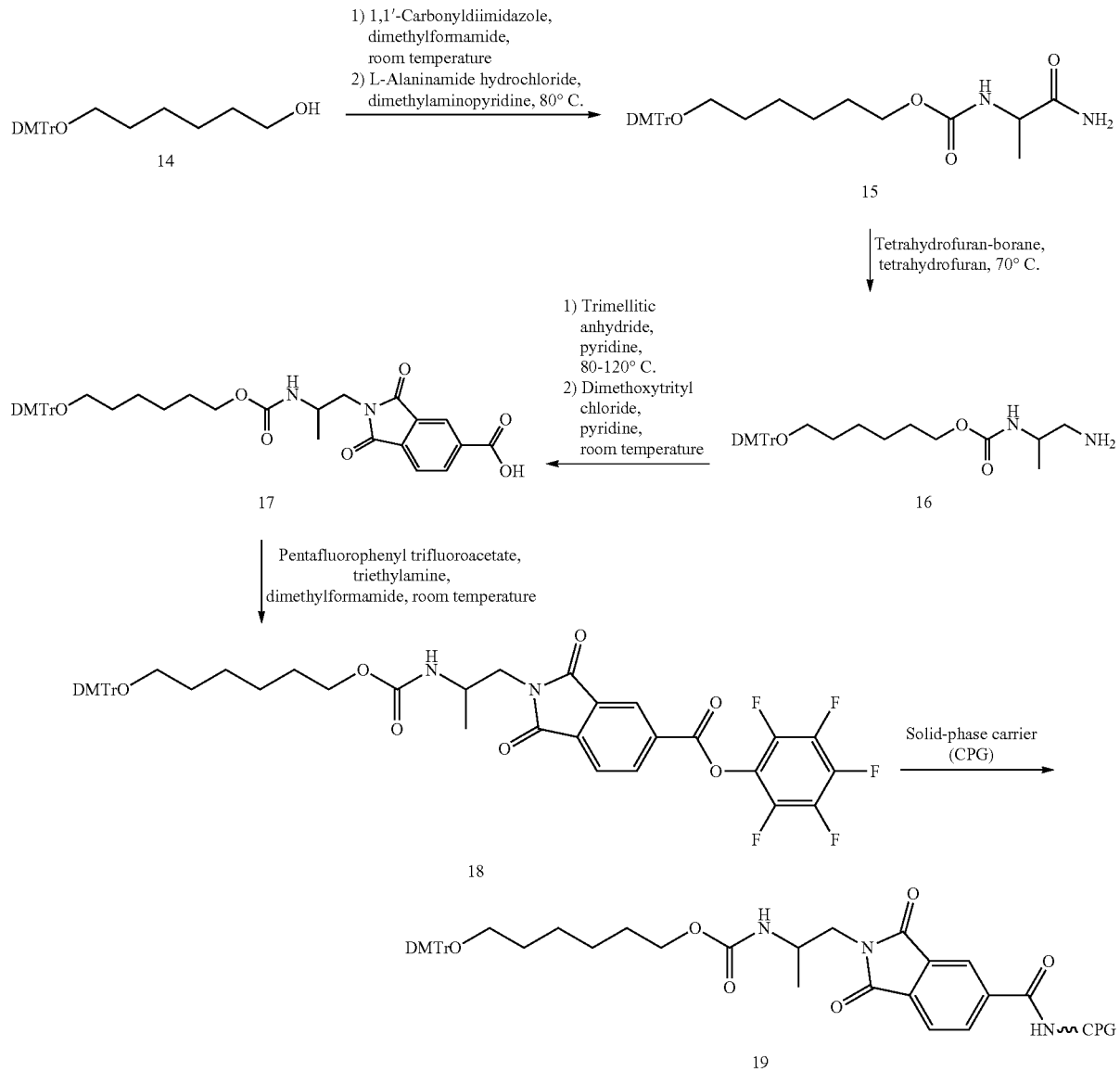

Scheme 3

N—(O-Dimethoxytrityl-6-hydroxyhexyloxycarbonyl)-L-alaninamide (compound 15)

In an argon atmosphere, 1.05 g (2.50 mmol) of 0-dimethoxytrityl-1,6-hexanediol (compound 14) was dissolved in 25 ml of dimethylformamide. To the solution, 1.74 ml (12.5 form, containing 0.3% pyridine) to obtain 720 mg (yield: 54%) of the title compound (compound 15) as a white foam.
ESI-MS Calculated: 557.2622 ($C_{31}H_{38}N_2O_6Na$ [M+Na]$^+$). Found: 557.2620. $^1$H NMR (270 MHz, DMSO-$d_6$) δ: 7.38-7.21 (m, 10H, DMT, NH), 7.07 (br d, 1H, NH, J=7.7 Hz), 6.94 (br s, 1H, NH), 6.89 (m, 4H, DMT), 3.91 (m, 1H, CH), 3.89 (t, 2H, CH$_2$, J=6.6 Hz), 3.73 (s, 6H, OMe×2), 2.95 (t, 2H, CH$_2$, J=6.5 Hz), 1.55-1.49 (m, 4H, CH$_2$×2), 1.32 (m, 2H, CH$_2$), 1.25 (m, 2H, CH$_2$), 1.18 (d, 3H, CH$_3$, J=7.2 Hz); $^{13}$C NMR (67.8 MHz, DMSO-d$_6$) δ: 174.93 (C), 158.34 (C), 156.20 (C), 145.63 (C), 136.43 (C), 129.94 (CH), 128.15 (CH), 128.01 (CH), 126.92 (CH), 113.49 (CH), 85.52 (C), 64.13 (CH$_2$), 63.06 (CH$_2$), 55.38 (CH$_3$), 50.13 (CH), 29.77 (CH$_2$), 28.98 (CH$_2$), 25.89 (CH$_2$), 25.58 (CH$_2$), 18.66 (CH$_3$).

(S)—O-Dimethoxytrityl-6-hydroxyhexyl 1-amino-2-propylcarbamate (compound 16)

In an argon atmosphere, 8.08 ml (1.1 mol/L, 9.0 mmol) of a tetrahydrofuran solution of borane was added to 40 ml of tetrahydrofuran, and the mixture was ice-cooled. A solution containing 1.60 g (3.00 mmol) of N—(O-dimethoxytrityl-6-hydroxyhexyloxycarbonyl)-L-alaninamide (compound 15) dissolved in 30 ml of tetrahydrofuran was added dropwise thereto. The reaction solution was stirred at 0° C. for 15 minutes and then heated at 70° C. for 1 hour. The reaction solution was brought back to room temperature. Then, 10 ml of a saturated aqueous solution of ammonium chloride was added thereto, and the mixture was stirred for 12 hours. 200 ml of ethyl acetate was added to the reaction solution, and the mixture was washed with 80 ml of water twice and 80 ml of saturated saline once and dried over sodium sulfate. The solution was concentrated under reduced pressure. Then, the residue was purified by silica gel column chromatography (elution solvent: ethanol-chloroform, containing 0.3% pyridine) to obtain 732 mg (yield: 47%) of the title compound (compound 16) as a colorless oil.

ESI-MS Calculated: 543.2829 (C$_{31}$H$_{40}$N$_2$O$_5$Na [M+Na]$^+$). Found: 543.2833. $^1$H NMR (270 MHz, DMSO-d$_6$) δ: 7.38-7.19 (m, 9H, DMT), 6.88 (m, 4H, DMT), 6.82 (br d, 1H, NH, J=7.6 Hz), 3.89 (t, 2H, CH$_2$, J=6.3 Hz), 3.73 (s, 6H, OMe×2), 3.38 (m, 1H, CH), 2.95 (t, 2H, CH$_2$, J=6.5 Hz), 2.48 (dd, 1H, CH$_2$a, J=6.4, 12.8 Hz), 2.43 (dd, 1H, CH$_2$b, J=5.9, 12.8 Hz), 1.55-1.48 (m, 4H, CH$_2$×2), 1.32 (m, 2H, CH$_2$), 1.25 (m, 2H, CH$_2$), 0.98 (d, 3H, CH$_3$, J=6.6 Hz); $^{13}$C NMR (67.8 MHz, DMSO-d$_6$) δ: 158.34 (C), 156.31 (C), 145.63 (C), 136.44 (C), 129.94 (CH), 128.14 (CH), 128.01 (CH), 126.91 (CH), 113.48 (CH), 85.53 (C), 63.77 (CH$_2$), 63.06 (CH$_2$), 55.38 (CH$_3$), 49.60 (CH), 47.39 (CH$_2$), 29.79 (CH$_2$), 29.04 (CH$_2$), 25.90 (CH$_2$), 25.64 (CH$_2$), 18.54 (CH$_3$).

(S)-1-[(4-Carboxyphthalimidyl-2-propyl)aminocarbonyl]oxy-O-(dimethoxytrityl)-6-hexanol (compound 17)

In an argon atmosphere, 270 mg (0.52 mmol) of (S)—O-dimethoxytrityl-6-hydroxyhexyl 1-amino-2-propylcarbamate (compound 16) and 110 mg (0.57 mmol) of trimellitic anhydride were dissolved in 20 ml of pyridine, and the solution was heated to reflux at 80° C. for 1 hour and further at 120° C. for 19 hours. The reaction solution was cooled to room temperature and then concentrated under reduced pressure. The residue was subjected to azeotropy with pyridine (5 ml×3). Then, the residue was dissolved in 10 ml of pyridine. To the solution, 264 mg (0.78 mmol) of dimethoxytrityl chloride was added, and the mixture was stirred at room temperature. After 1 hour, 100 mg (0.30 mmol) of dimethoxytrityl chloride was further added to the reaction solution, and the mixture was stirred at room temperature for additional 1 hour. 1 ml of ethanol was added to the reaction solution, and the mixture was then concentrated under reduced pressure. The residue was dissolved in 70 ml of chloroform. The solution was washed with 25 ml of water twice and 25 ml of saturated saline once and dried over sodium sulfate. The solution was concentrated under reduced pressure, followed by azeotropy with 5 ml of toluene. The residue was purified by silica gel column chromatography (elution solvent: ethanol-chloroform, containing 0.3% pyridine) to obtain 262 mg (pyridine salt, yield: 65%) of the title compound (compound 17) as a white foam.

ESI-MS Calculated: 693.2818 (C$_{40}$H$_{41}$N$_2$O$_9$ [M−H]$^−$). Found: 693.2820. $^1$H NMR (270 MHz, DMSO-d$_6$) δ: 8.58 (m, 2H, Py), 8.32 (d, 1H, Phth, J=7.7 Hz), 8.22 (s, 1H, Phth), 7.95 (d, 1H, Phth, J=7.7 Hz), 7.78 (m, 1H, Py), 7.38 (m, 2H, Py), 7.37-7.19 (m, 9H, DMT), 7.04 (br d, 1H, NH, J=8.8 Hz), 6.90-6.85 (m, 4H, DMT), 3.89 (m, 1H, CH), 3.75 (m, 1H, CH), 3.73 (s, 6H, OCH$_3$×2), 3.71 (m, 1H, CH), 3.58 (m, 2H, CH$_2$), 2.94 (t, 2H, CH$_2$, J=6.3 Hz), 1.50 (m, 2H, CH$_2$), 1.34 (m, 2H, CH$_2$), 1.24 (m, 2H, CH$_2$), 1.14 (m, 2H, CH$_2$), 1.08 (d, 3H, CH$_3$, J=6.9 Hz); $^{13}$C NMR (67.8 MHz, DMSO-d$_6$) δ: 167.09 (C), 167.08 (C), 165.73 (C), 157.87 (C), 155.82 (C), 149.51 (CH, Py), 145.18 (C), 136.03 (CH, Py), 135.98 (C), 135.02 (CH), 134.82 (C), 131.99 (C), 129.48 (CH), 127.67 (CH), 127.56 (CH), 126.44 (CH), 123.81 (CH, Py), 123.18 (CH), 122.86 (CH), 113.01 (CH), 85.06 (C), 63.34 (CH$_2$), 62.56 (CH$_2$), 54.90 (CH$_3$), 45.12 (CH), 43.08 (CH$_2$), 29.28 (CH$_2$), 28.42 (CH$_2$), 25.32 (CH$_2$), 24.96 (CH$_2$), 17.76 (CH$_3$).

(S)-1-[(4-Pentafluorophenoxycarbonylphthalimidyl-2-propyl)aminocarbonyl]oxy-O-(dimethoxytrityl)-6-hexanol (compound 18)

183 mg (yield: 71%) of the title compound (compound 18) was obtained as a white foam by the same treatment as in the synthesis of compound 5a using 232 mg (0.30 mmol) of (S)-1-[(4-carboxyphthalimidyl-2-propy)aminocarbonyl]oxy-O-(dimethoxytrityl)-6-hexanol (compound 17, pyridine salt) as a starting material.

ESI-MS Calculated: 883.2624 (C$_{46}$H$_{41}$N$_2$O$_9$F$_5$Na [M+Na]$^+$). Found: 883.2641. $^1$H NMR (270 MHz, DMSO-d$_6$) δ: 8.55 (d, 1H, Phth, J=7.7 Hz), 8.45 (s, 1H, Phth), 8.10 (d, 1H, Phth, J=7.7 Hz), 7.36-7.18 (m, 9H, DMT), 7.08 (br d, 1H, NH, J=7.2 Hz), 6.89-6.83 (m, 4H, DMT), 3.92 (m, 1H, CH), 3.77 (m, 1H, CH), 3.72 (s, 6H, OCH$_3$×2), 3.68 (m, 1H, CH), 3.61 (m, 2H, CH$_2$), 2.93 (t, 2H, CH$_2$, J=6.5 Hz), 1.49 (m, 2H, CH$_2$), 1.33 (m, 2H, CH$_2$), 1.23 (m, 2H, CH$_2$), 1.13 (m, 2H, CH$_2$), 1.10 (d, 3H, CH$_3$, J=6.9 Hz).

revMe Linker-CPG Solid-Phase Carrier (Compound 19)

The title compound (compound 19) (35.0 μmol/g) was obtained by the same treatment as in the synthesis of compound 6a using 103 mg (0.12 mmol) of (S)-1-[(4-pentafluorophenoxycarbonylphthalimidyl-2-propypaminocarbonyl]oxy-O-(dimethoxytrityl)-6-hexanol (compound 18) as a starting material.

Example 5

Synthesis of revMeOH Linker-CPG Solid-Phase Carrier (Compound 23)

A solid-phase carrier for 3' amination modification was synthesized according to the following scheme 4:

Scheme 4

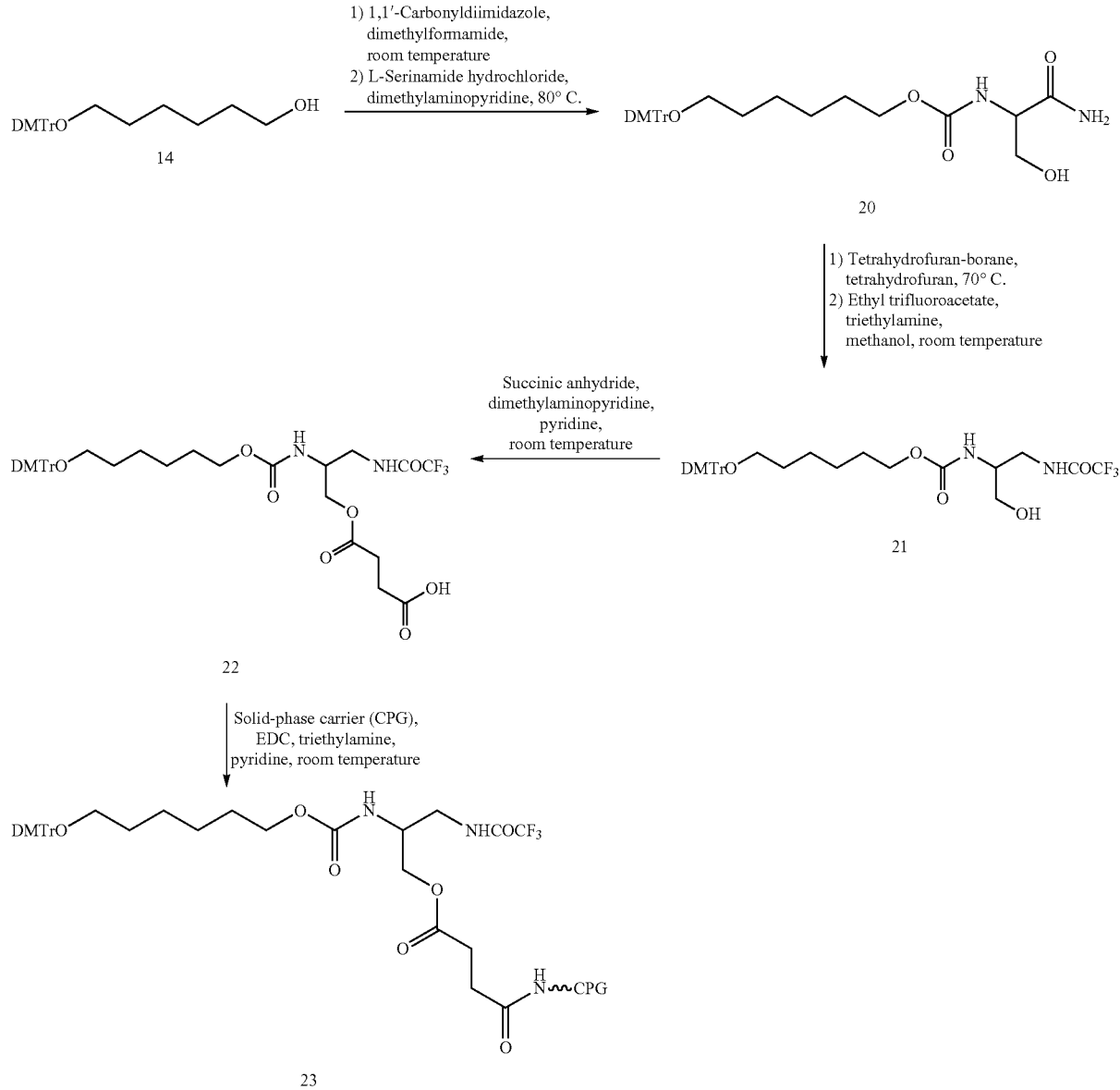

N—(O-Dimethoxytrityl-6-hydroxyhexyloxycarbonyl)-L-serinamide (compound 20)

In an argon atmosphere, 1.34 g (3.20 mmol) of O-dimethoxytrityl-1,6-hexanediol (compound 14) was dissolved in 40 ml of dimethylformamide. To the solution, 2.23 ml (16.0 mmol) of triethylamine and 570 mg (3.52 mmol) of 1,1'-carbonyldiimidazole were added, and the mixture was stirred at room temperature for 3 hours. Subsequently, 675 mg (4.80 mmol) of L-serinamide hydrochloride and 39 mg (0.32 mmol) of dimethylaminopyridine were added to the reaction solution, and the mixture was stirred at 80° C. for 2 days. 250 ml of ethyl acetate was added to the reaction solution, and the mixture was washed with 100 ml of water four times and 100 ml of saturated saline once and dried over sodium sulfate. The solution was concentrated under reduced pressure. Then, the residue was purified by silica gel column chromatography (elution solvent: ethanol-chloroform, containing 0.3% pyridine) to obtain 685 mg (yield: 39%) of the title compound (compound 20) as a white foam.

ESI-MS Calculated: 573.2571 ($C_{31}H_{38}N_2O_7Na$ [M+Na]$^+$). Found: 573.2569. $^1$H NMR (270 MHz, DMSO-$d_6$) δ: 7.41-7.19 (m, 10H, DMT, NH), 7.06 (br s, 1H, NH), 6.89 (m, 4H, DMT), 6.82 (br d, 1H, NH, J=8.3 Hz), 4.81 (t, 1H, OH, J=5.6 Hz), 3.95 (m, 1H, CH), 3.91 (t, 2H, CH$_2$, J=6.6 Hz), 3.73 (s, 6H, OMe×2), 3.56 (m, 2H, CH$_2$), 2.95 (t, 2H, CH$_2$, J=6.3 Hz), 1.53 (m, 4H, CH$_2$×2), 1.29 (m, 4H, CH$_2$×2); $^{13}$C NMR (67.8 MHz, DMSO-$d_6$) δ: 172.17 (C), 157.95 (C), 156.05 (C), 145.25 (C), 136.04 (C), 129.57 (CH), 127.78 (CH), 127.63 (CH), 126.55 (CH), 113.11 (CH), 85.13 (C), 63.91 (CH$_2$), 62.67 (CH$_2$), 61.84 (CH$_2$), 56.94 (CH), 55.00 (CH$_3$), 29.39 (CH$_2$), 28.57 (CH$_2$), 25.53 (CH$_2$), 25.19 (CH$_2$).

(R)—O-Dimethoxytrityl-6-hydroxyhexyl [1-hydroxy-3-(trifluoroacetyl)amino]-2-propylcarbamate (compound 21)

In an argon atmosphere, 110 mg (0.20 mmol) of N-(O-dimethoxytrityl-6-hydroxyhexyloxycarbonyl)-L-serinamide (compound 20) was dissolved in 10 ml of tetrahydrofuran, and the solution was ice-cooled. To the solution, 0.50 ml (1.2 mol/L, 0.60 mmol) of a tetrahydrofuran solution of borane was added. The reaction solution was stirred at 0° C. for 15 minutes and then heated at 70° C. for 1 hour. The reaction solution was brought back to room temperature. Then, 1 ml of a saturated aqueous solution of ammonium chloride was added thereto, and the mixture was stirred for 1 hour. 40 ml of ethyl acetate was added to the reaction solution, and the mixture was washed with 15 ml of water twice and 15 ml of saturated saline once and dried over sodium sulfate. The solution was concentrated under reduced pressure. Then, the residue was dissolved in 5.0 ml of methanol. To the solution, 0.084 ml (0.60 mmol) of triethylamine and 0.048 ml (0.40 mmol) of ethyl trifluoroacetate were added, and the mixture was stirred at room temperature for 1 hour. The reaction solution was concentrated under reduced pressure. Then, the residue was purified by silica gel column chromatography (elution solvent: ethanol-chloroform, containing 0.3% pyridine) to obtain 88 mg (yield: 82%) of the title compound (compound 21) as a white foam.

ESI-MS Calculated: 655.2602 ($C_{33}H_{39}N_2O_7F_3Na$ [M+Na]$^+$). Found: 655.2602. $^1$H NMR (270 MHz, DMSO-$d_6$) δ: 9.34 (br s, 1H, NH), 7.41-7.18 (m, 9H, DMT), 6.89 (m, 4H, DMT), 6.82 (br d, 1H, NH, J=8.9 Hz), 4.76 (br s, 1H, OH), 3.89 (m, 2H, CH$_2$), 3.73 (s, 6H, OMe×2), 3.67 (m, 2H, CH$_2$), 3.33 (m, 2H, CH$_2$), 3.20 (m, 1H, CH$_2$), 2.94 (t, 2H, CH$_2$, J=6.3 Hz), 1.52 (m, 4H, CH$_2$×2), 1.27 (m, 4H, CH$_2$×2); $^{13}$C NMR (67.8 MHz, DMSO-$d_6$) δ: 157.96 (C), 156.49 (C, q, J=36.3 Hz), 156.16 (C), 145.26 (C), 136.05 (C), 129.57 (CH), 127.77 (CH), 127.63 (CH), 126.55 (CH), 115.93 (CF$_3$, q, J=288.3 Hz), 113.10 (CH), 85.13 (C), 63.68 (CH$_2$), 62.69 (CH$_2$), 61.24 (CH$_2$), 54.99 (CH$_3$), 51.90 (CH), 40.66 (CH$_2$), 29.38 (CH$_2$), 28.59 (CH$_2$), 25.54 (CH$_2$), 25.19 (CH$_2$).

(R)—O-Dimethoxytrityl-6-hydroxyhexyl [1-hydroxy-3-(trifluoroacetyl)amino]-2-propylcarbamate succinic acid ester (compound 22)

In an argon atmosphere, 168 mg (0.27 mmol) of (R)—O-dimethoxytrityl-6-hydroxyhexyl [1-hydroxy-3-(trifluoroacetyl)amino]-2-propylcarbamate (compound 21) was dissolved in 5 ml of pyridine. To the solution, 81 mg (0.81 mmol) of succinic anhydride and 33 mg (0.27 mmol) of dimethylaminopyridine were added, and the mixture was stirred at room temperature for 6 hours. 1 ml of water was added to the reaction solution, and the mixture was then concentrated under reduced pressure. 40 ml of chloroform was added to the residue, and the mixture was washed with 15 ml of a saturated aqueous solution of potassium dihydrogen phosphate twice and 15 ml of saturated saline once and dried over sodium sulfate. The solution was concentrated under reduced pressure. Then, the residue was purified by silica gel column chromatography (elution solvent: ethanol-chloroform, containing 0.3% pyridine) to obtain 190 mg (yield: 96%) of the title compound (compound 22) as a white foam.

ESI-MS Calculated: 755.2762 ($C_{37}H_{43}N_2O_{10}F_3Na$ [M+Na]$^+$). Found: 755.2764. $^1$H NMR (270 MHz, DMSO-$d_6$) δ: 12.25 (br s, 1H, COOH), 9.45 (br d, 1H, NH, J=5.3 Hz), 7.41-7.18 (m, 9H, DMT), 7.15 (br d, 1H, NH, J=8.2 Hz), 6.89 (m, 4H, DMT), 4.04 (m, 1H, CH), 3.93-3.87 (m, 4H, CH$_2$×2), 3.73 (s, 6H, OMe×2), 3.29 (m, 2H, CH$_2$), 2.94 (t, 2H, CH$_2$, J=6.3 Hz), 2.49-2.47 (m, 4H, CH$_2$×2), 1.52 (m, 4H, CH$_2$×2), 1.27 (m, 4H, CH$_2$×2); $^{13}$C NMR (67.8 MHz, DMSO-$d_6$) δ: 173.36 (C), 171.91 (C), 157.96 (C), 156.58 (C, q, J=36.3 Hz), 156.09 (C), 145.26 (C), 136.05 (C), 129.57 (CH), 127.77 (CH), 127.63 (CH), 126.55 (CH), 115.88 (CF$_3$, q, J=287.7 Hz), 113.10 (CH), 85.13 (C), 63.88 (CH$_2$), 63.57 (CH$_2$), 62.68 (CH$_2$), 54.99 (CH$_3$), 48.88 (CH), 40.30 (CH$_2$), 29.39 (CH$_2$), 28.64 (CH$_2$), 28.58 (CH$_2$), 28.55 (CH$_2$), 25.51 (CH$_2$), 25.17 (CH$_2$).

revMeOH Linker-CPG Solid-Phase Carrier (Compound 23)

In a glass vial, 146 mg (0.20 mmol) of (R)—O-dimethoxytrityl-6-hydroxyhexyl [1-hydroxy-3-(trifluoroacetyl)amino]-2-propylcarbamate succinic acid ester (compound 22) was dissolved in 8 ml of pyridine. To the solution, 350 mg (40.0 μmol) of LCAA-CPG, 383 mg (2.0 mmol) of EDC, 80 μl of triethylamine, and 12 mg (0.10 mmol) of dimethylaminopyridine were added, and the mixture was vigorously shaken at room temperature for 27 hours. The CPG was washed with pyridine (10 ml×4) and methylene chloride (10 ml×2) and then dried under reduced pressure at room temperature for 1.5 hours. Subsequently, 8 ml of a capping solution (mixed solution of pyridine and acetic anhydride (9:1) containing 0.1 M dimethylaminopyridine) was added to the CPG, and the mixture was vigorously shaken at room temperature for 2 hours. The CPG was washed with pyridine (10 ml×4) and methylene chloride (10 ml×2) and then dried under reduced pressure to obtain the title compound (compound 23) (44.9 μmol/g).

Synthesis Example 5

Synthesis of Deoxyoligonucleotide Probe

The solid-phase carriers for 3' amination modification of Example 4 (revMe linker-CPG) and Example 5 (revMeOH linker-CPG) as starting materials were treated in the same way as in Synthesis Example 2. On each solid-phase carrier, deoxynucleoside 3'-phosphoramidites (Glen Research Corp.) were sequentially condensed according to the sequence to synthesize a 3'-aminated oligonucleotide with a 5-base strand length comprising the amino linker of Example 4 or 5.

Sequence of 5-base 3'-aminated oligonucleotide (T5-X; X=revMe or revMeOH):

```
5' TTTTT-X 3'
(X = revMe or revMeOH)
```

Use Example 7

Confirmation of Stability Under Alkaline Conditions

Figure 9:
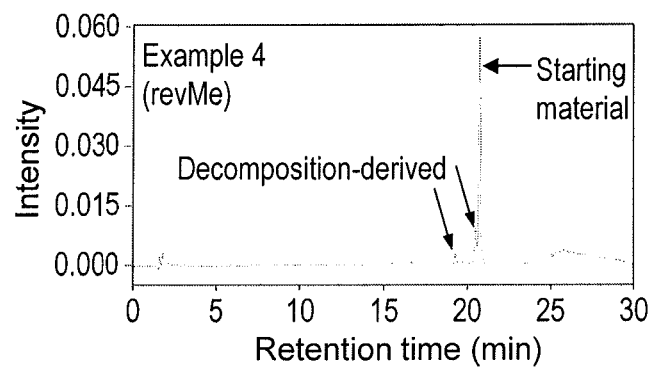
FIG. 9 is a diagram showing results of reverse-phase HPLC analysis of a reaction solution after concentrated ammonia water treatment (heating at 55° C. for 16 hours) of a 5-base oligonucleotide (T5-X) synthesized using a solid-phase carrier for 3' amination modification of Example 4 or 5.
Figure 9:
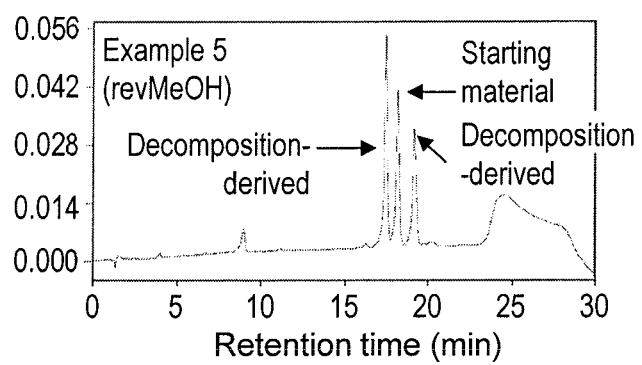
Figure 10:
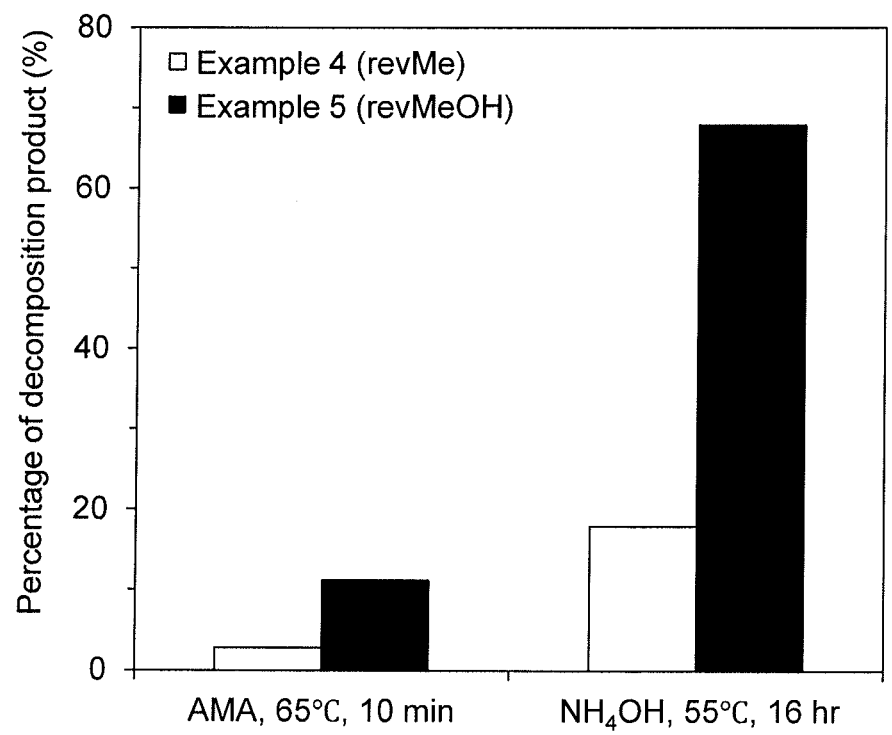
FIG. 10 is a diagram showing the ratio (%) of the amount of T5-X decomposed by AMA solution treatment or concentrated ammonia water treatment to the total amount of the 3'-aminated oligonucleotide (T5-X) after the AMA solution treatment or the concentrated ammonia water treatment.

Each aminated oligonucleotide comprising the amino linker of Example 4 (revMe linker-CPG) or Example 5 (revMeOH linker-CPG) was evaluated for its stability under alkaline conditions in the same way as in Use Example 1 or 2. FIG. 9 shows HPLC analysis results of the reaction solution of the synthesized aminated oligonucleotide treated with concentrated ammonia water. FIG. 10 shows the ratio (%) of the amount of T5-X decomposed by AMA solution treatment or concentrated ammonia water treatment to the total amount of the 3'-aminated oligonucleotide (T5-X).

Alkaline Treatment Conditions for 3'-Aminated Oligonucleotide:

AMA solution [40% methylamine:concentrated ammonia water (1:1), 65° C., 10 min]

Concentrated ammonia water [concentrated ammonia water, 55° C., 16 hr]

As shown in FIG. 9, a decomposition-derived peak was detected due to the concentrated ammonia water treatment in the 5-base 3'-aminated oligonucleotide (T5-revMe) comprising the amino linker of Example 4. Also, a decomposition-derived peak was detected due to the concentrated ammonia water treatment in the 5-base 3'-aminated oligonucleotide (T5-revMeOH) comprising the amino linker of Example 5, but had intensity larger than that of T5-revMe.

As shown in FIG. 10, the 5-base 3'-aminated oligonucleotide (T5-revMeOH) comprising the amino linker of Example 5 was decomposed approximately 11% by the AMA solution treatment which was the 3'-aminated oligonucleotide excision condition from the solid-phase carrier. Also, the 5-base 3'-aminated oligonucleotides comprising the amino linker of Example 4 or 5 were decomposed approximately 18% and approximately 68%, respectively, by the concentrated ammonia water treatment.

These results suggest that the 3'-aminated oligonucleotide represented by the formula I of the present invention exhibits reduced stability against alkaline treatment when having a branch group or a substituent in $R_2$. This result may be attributed to the reactivity of transacylation reaction in the alkaline treatment. As with Example 1 (revH) and Example 2 (revPro) wherein $R_2$ is an unsubstituted linear divalent aliphatic hydrocarbon group, even transacylation yields a transacylation product having the same structure as that before the transfer without causing structural change because of the symmetry of $R_2$. This apparently yields no decomposition product. By contrast, as with Example 4 (revMe) and Example 5 (revMeOH) wherein $R_2$ is a branched (or substituted) divalent group, the transacylation product is formed as a decomposition product. Alternatively, as with Example 5 (revMeOH) wherein the branch group or the substituent in $R_2$ is a bulky group with large steric hindrance, conformational equilibrium seems to largely shift toward anti-conformation and therefore further promote transacylation reaction.

INDUSTRIAL APPLICABILITY

The present invention can enhance the efficiency of 3'-end chemical modification of oligonucleotides. As a result, nucleic acid drugs or probes for gene detection can be synthesized at low cost.

All publications, patents, and patent applications cited herein are incorporated herein by reference in their entirety.

The invention claimed is:

1. An aminated oligonucleotide represented by the following formula I:

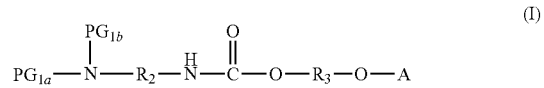

(I)

wherein
PG$_{1a}$ and PG$_{1b}$ are each independently a hydrogen atom or a protective group for the amino group, or
PG$_{1a}$ and PG$_{1b}$ together form a protective group for the amino group;
$R_2$ is ethylene;
$R_3$ is an unsubstituted divalent aliphatic hydrocarbon group having 2 to 15 members in the main chain; and
A is an oligonucleotide.

2. A solid-phase carrier represented by the following formula IV:

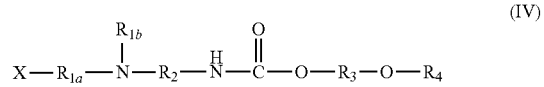

(IV)

wherein

X is a carrier material;

$R_{1a}$ is a direct bond or a divalent group, and $R_{1b}$ is a hydrogen atom, or $R_{1a}$ and $R_{1b}$ together form a group bound to X and the amino group;

$R_2$ is ethylene;

$R_3$ is an unsubstituted divalent aliphatic hydrocarbon group having 2 to 15 members in the main chain; and $R_4$ is a protective group for the hydroxy group.

3. The solid-phase carrier according to claim 2, wherein $R_4$ is a trityl group or a monosubstituted or disubstituted trityl group.

4. An aminated oligonucleotide probe represented by the following formula Ib:

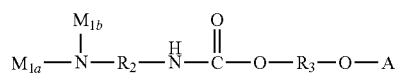

(Ib)

wherein $M_{1a}$ and $M_{1b}$ are each independently a hydrogen atom or a group derived from a probe molecule, or $M_{1a}$ and $M_{1b}$ together form a group derived from a probe molecule;

$R_2$ is ethylene;

$R_3$ is an unsubstituted divalent aliphatic hydrocarbon group having 2 to 15 members in the main chain; and A is an oligonucleotide.

5. The aminated oligonucleotide according to claim 1, wherein $R_3$ is hexylene.

6. The solid-phase carrier according to claim 2, wherein $R_3$ is hexylene.

7. The aminated oligonucleotide probe according to claim 4, wherein $R_3$ is hexylene.

8. The aminated oligonucleotide according to claim 1, wherein $R_3$ is an unsubstituted divalent aliphatic group having 2 to 6 members in the main chain.

9. The solid-phase carrier according to claim 2, wherein $R_3$ is an substituted divalent aliphatic group having 2 to 6 members in the main chain.

10. The aminated oligonucleotide probe according to claim 4, wherein $R_3$ is an unsubstituted divalent aliphatic group having 2 to 6 members in the main chain.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial
<220> FEATURE:
<223> OTHER INFORMATION: synthetic DNA

<400> SEQUENCE: 1
tcttccaagc aattccaatg aaagc                                          25

<210> SEQ ID NO 2
<211> LENGTH: 20
<212> TYPE: RNA
<213> ORGANISM: Artificial
<220> FEATURE:
<223> OTHER INFORMATION: synthetic RNA

<400> SEQUENCE: 2
aaaccucuuc caagcaauuc                                                20
```